(12) United States Patent
Weng et al.

(10) Patent No.: US 8,414,615 B2
(45) Date of Patent: Apr. 9, 2013

(54) SPINAL DYNAMIC STABILIZATION DEVICE, SURGICAL METHOD UTILIZING THEREOF AND CLAMPING APPARATUS

(75) Inventors: Yu Shih Weng, Pingtung County (TW); Ting-Hui Chiu, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 265 days.

(21) Appl. No.: 12/650,342

(22) Filed: Dec. 30, 2009

(65) Prior Publication Data
US 2010/0168794 A1 Jul. 1, 2010

(30) Foreign Application Priority Data

Dec. 30, 2008 (TW) ................ 97151395 A

(51) Int. Cl.
*A61B 17/70* (2006.01)
(52) U.S. Cl.
USPC .......................................... 606/249
(58) Field of Classification Search ............ 606/248, 606/249
See application file for complete search history.

(56) References Cited

U.S. PATENT DOCUMENTS

| | | |
|---|---|---|
| 2006/0008983 A1 | 1/2006 | Yeh |
| 2007/0032790 A1 | 2/2007 | Aschmann et al. |
| 2007/0161992 A1 | 7/2007 | Kwak et al. |
| 2007/0173832 A1 | 7/2007 | Tebbe et al. |
| 2007/0276372 A1 | 11/2007 | Malandain et al. |
| 2008/0071380 A1 | 3/2008 | Sweeney |
| 2008/0086212 A1* | 4/2008 | Zucherman et al. ....... 623/17.11 |
| 2008/0294263 A1* | 11/2008 | Altarac et al. ............. 623/17.16 |

FOREIGN PATENT DOCUMENTS

| | | |
|---|---|---|
| CN | 1460453 A | 12/2003 |
| CN | 101146494 | 3/2008 |
| CN | 101227867 | 7/2008 |

\* cited by examiner

*Primary Examiner* — Ellen C Hammond

(57) ABSTRACT

A spinal dynamic stabilization device is provided, including at least a main portion, at least a supporting structure, and a sliding bar. The main portion includes a guiding groove. The supporting structure includes two wing portions. The wing portions pivot on the main portion. The sliding bar connects to the supporting structure and moves in the guiding groove. When the sliding bar moves in the guiding groove, the wing portions expand rotatably toward the adjacent vertebrae of the spine of the patient by the sliding bar.

37 Claims, 23 Drawing Sheets

SPINAL DYNAMIC STABILIZATION DEVICE, SURGICAL METHOD UTILIZING THEREOF AND CLAMPING APPARATUS

This application claims priority of Taiwan Patent Application No. 97151395, filed on Dec. 30, 2008.

BACKGROUND OF THE INVENTION

1. Field of the Invention

The invention relates to a spinal dynamic stabilization device which is positioned between adjacent vertebrae, more particularly adjacent spinal process, for decompressing nerves through distracting narrowed spinal canal or foramen, relieving back pain. The invention also discloses methods and devices for redistribution of compression loads to minimize occurrence of bone fracture.

2. Description of the Related Art

In the U.S., the largest spine device and apparatus market in the world, it is estimated that over two million patients visit doctors every year because of lower back pain. Of those, about 40 percent have degenerative disc disease, DDD. The number of patients in the world with lower back pain is expected to increase due to the aging world population. According to a recent forecast, up till 2009, over 51 millions people in the US will be expected to solve their spine problems by surgical intervention, spinal fusion surgery, for example. Decompression and fusion surgery are current surgical standards for lower back pain treatment. In general, decompression surgeries, laminectomy and distectomy, for example, are adapted as primary surgical interventions to relieve pain for patients in relative early stage of disc degeneration. For patients suffered from more severe spinal instability, spinal fusion surgery is clinically applied as final and gold standard to stabilized spinal column by fusion of two spinal columns.

Laminectomy is the process wherein the laminar of a spine is partially or totally removed to decompress nerves, thus preserving spinal motion in patients during the early stages of a degenerative spine. However, tissue removal during decompression can lead to improper spine biomechanics which might further facilitate disc degeneration. In contrast to decompression surgery, fusion surgery is clinically chosen as final solutions to help patients stabilized their degenerative spine. However, fusion surgery are not recognized as best solutions for patients due to some concerns that include: (1) limited movement of adjacent vertebrae; (2) acceleration of adjacent level degeneration, wherein the mechanics of the spine changed after spinal columns are fused and motions on the adjacent segment of increases to compensate for the fused segment; and (3) incomplete fusion resulting in pseudoarthrosis and easy fracturing, wherein in the worst cases, the implant cage is required to be removed.

Thus, non-fusion surgical techniques have been disclosed. Generally, dynamic stabilization systems such as the interspinous process spacer and pedicle screw-based systems have been developed to assist in preserving motion for patients after surgery.

Meanwhile, with increased advances in the medical field, minimally invasive surgery has become a trend. Compared with traditional surgery, advantages of minimally invasive surgery include: smaller incisions; decreased blood loss during surgery; and decreased probability for complications. Additionally, the amount of time required for surgery and recovery time are considered to be shortened once device and instrument is well-designed.

U.S. Patent No. 20070161992 discloses a vertebrae implant device with a pair of pivoting S-shaped arms. The arms in a closed state are implanted into adjacent vertebrae. After implantation, the arms are expanded to maintain a height between the adjacent vertebrae. However, the device is applied by traditional surgery methods, thus, resulting incisions are relatively large.

U.S. Patent No. 20070032790 discloses a device treating stenosis with an insertion element and a sleeve. The insertion element comprises one end, and the sleeve comprises the other end. Before implantation, two arms in a closed state are disposed in the sleeve. After implantation, the arms are expanded.

U.S. Patent No. 20060008983 discloses a device made of PU. Before implantation, the device is not filled with fluid. After implantation, gas or liquid is filled into the device, and the device expands into an H-shape. However, studies show that the strength and the fixation efficiency of the device are unsatisfactory.

U.S. Patent No. 20070276372 discloses a surgery method and a device utilizing the same. An axle device with procedure ends is implanted into a body via skin. After implantation, one end is pushed toward one direction, and the other end is pushed toward the other end to stabilize the spine.

U.S. Patent No. 20070173832 discloses MIS-based surgery methods, wherein a device is expanded and implanted.

U.S. Patent No. 2006008983 discloses a spine stabilization device with a supporting portion. When the supporting portion is implanted in the vertebra, the arms are pushed from two sides or are rotated to expand.

BRIEF SUMMARY OF THE INVENTION

The invention provides methods for distracting adjacent spinal vertebrae, more particularly related to spinal process, and redistributes loads by introducing multiple contacts between devices and spinal vertebrae, or spinous processes, as well during spinal motion. Each spinal vertebrae comprises a spinal process. The invention can be implemented with either open or percutaneous approach. Moreover, it can also be combined with decompression surgery, laminectomy, disectomy, or fusion surgery, for example, to provide better posterior stabilization. The steps comprise: providing a spinal dynamic stabilization device, the spinal dynamic stabilization device comprising a main portion with saddle portion, a stabilizing portion with two arm portions which pivot to each other, and an connecting portion movably connect the main portion and stabilizing portion; inserting spinal dynamic stabilization device in a closed state; pushing the main portion or insertion portion toward stabilizing portion to open stabilizing portion. Opening direction of stabilizing portion is rotatable from posterior side toward anterior side of spine. Plane generated during expanding stabilizing portion is perpendicular to inserting direction of device.

The opened construct provides multiple contacts between construct and adjacent vertebra, particularly adjacent spinal processes, during spinal motion to redistribute loads. Those contacts include anterior contact(s) and posterior contact(s) in terms of vertical axis of sagittal plane. Vertical distance between two opposite anterior contacts of device, generating from contacts between device with upper process and lower process, respectively, is different from one generated from posterior side of process when spine motion is further extension. In some better implementations, anterior contact is higher than posterior contact. The former is used to provide first load-bearing site, and the latter is used to provide second load-bearing site to redistribute compressive loads. Those contacts on anterior portion of device can move relatively that result from damping property of device. Tensile strength of vertebrae can be further minimized when device is implanted toward anterior side of spine. Also, contacts on a side of process minimize occurrence of fracture of spinous process when compression load or moment is applied frequently. Moreover, one contact between device and adjacent processes can move elastically to another opposite contact. The device is also composed of damping portion to absorb a certain amount of loads. Stabilizing portion of device can be flexible to avoid limiting spine motion.

Note that when the depression supports the spinal process, at least one contact point is generated.

Note that the adjacent vertebrae have a sagittal plane, and the stabilizing portion rotatably expand toward the sagittal plane.

The invention provides a method for distracting adjacent spinal vertebrae. The adjacent vertebrae have a sagittal plane. Each spinal vertebrae comprises a spinal process. The steps comprise: providing a spinal dynamic stabilization device, the spinal dynamic stabilization device comprising a main portion, a stabilizing portion with two arm portions, pivoting on the main portion, and an insertion portion movably connecting to the main portion; implanting the spinal dynamic stabilization device in a closed state between the adjacent spinal vertebrae; pushing the insertion portion into the main portion to open the stabilizing portion toward the sagittal plane; and propping the adjacent spinal vertebrae with the arm portions.

Note that the main portion further comprises a pivot portion to connect to the main portion and the stabilizing portion.

Note that the main portion and the stabilization portion are detachable.

Note that connection between the main portion and the stabilizing portion is not linear, or train-like arrangement.

Note that connection between the main portion and the stabilizing portion include an angle, the angle is not equal to zero.

The invention provides a spinal dynamic stabilization device implanting adjacent vertebrae to distract the adjacent vertebrae. The adjacent vertebrae have a sagittal plane. The spinal dynamic stabilization device comprises at least a main portion, at least a stabilizing portion and at least an insertion portion. The main portion comprises a guiding groove. The stabilizing portion comprises two arm portions. The insertion portion movably connects to the main portion. When the insertion portion moves in the guiding groove relatively to main portion, the stabilizing portion expands rotatably toward the sagittal plane.

Note that the main portion further comprises at least a pivot portion to connect the stabilizing portions.

Note that the stabilizing portions respectively comprise a pivot portion, the pivot portions respectively rotatably connect to the main portion.

Note that at least one of the pivot portions is not disposed on center of the device.

Note that the device further comprises at least a pivot portion to connect the stabilizing portions. The pivoting portion facilitate transformation of the device from closed state to opened state Note that at least one of the pivot portions is disposed to near the edge of the main portion.

Note that at least one of the pivot portions is hollow.

Note that at least one of the pivot portions is slidable for the main portion.

Note that the device further comprises locking means to engage the main portion and the stabilizing portion.

Note that at least one of the pivot portions is made of flexible material.

Note that the main portion further comprises an opening, and the stabilizing portions expand pivotally away from the main portion when main portion move relative closer to stabilizing portion.

Note that the main portion further comprises an opening. When the insertion portion moves in the guiding groove relatively to the main portion, the arm portions open rotatably from the opening.

Note that the opening is perpendicular to a moving direction of the insertion portion along the cross-section of the main portion.

Note that the cross-section of the main portion is C-shape.

Note that the main portion is a sheet-like structure.

Note that the stabilizing portion is expandable.

Note that the main portion comprises a cone portion disposed on one end of main portion.

Note that the stabilizing portion is made of a compressible and damping material.

Note that the stabilizing portion is made of polymer or metal.

Note that the arm portions of the stabilizing portion is curve shaped.

Note that at least one of the arm portions of stabilizing portion is connected to the side of the spinal processes.

Note that when the number of the stabilizing portion is two, the stabilizing portion is pivoted to each other.

Note that the stabilizing portion is U, or H shaped.

Note that the main portion further comprises an opening, and when the insertion portion moves in the guiding groove relatively to main portion, the arm portions protrude from the opening.

Note that the insertion portion comprises an engaging portion, the engaging portion is lockable.

Note that the engaging portion comprises four portions, one end of the portions is connected to each other, the portions are arranged to generate a gap therebetween.

The invention provides a spinal dynamic stabilization device implanting adjacent vertebrae to distract the adjacent vertebrae. The adjacent vertebrae have a sagittal plane. The spinal dynamic stabilization device comprises at least a main portion, at least a stabilizing portion, and at least an insertion portion. The main portion comprises a guiding groove and a depression. The stabilizing portion comprises two arm portions and a connecting portion between the arm portions, and the stabilizing portion is pivoted on the main portion. The insertion portion movably connects to the main portion. When the stabilizing portion covers the main portion, the depression is higher than the connecting portion.

Note that the insertion portion engages the main portion and the stabilizing portion.

Note that the insertion portion opens the stabilizing portions.

Note that the insertion portion engages the main portion and the stabilizing portions.

Note that the depression supports the spinal process, and at least one contact point is generated.

Note that the adjacent vertebrae have a sagittal plane, and the stabilizing portion rotatably expand toward the sagittal plane.

Note that an interval distance between the arm portions of the stabilizing portion is larger than the width of the depression.

The invention provides a clamping apparatus to hold a spinal dynamic stabilization device to prop adjacent vertebrae. The clamping apparatus comprises a handle element, a clamping element, a connecting member and a guiding tube. The handle element and the clamping element are connected by the connecting member. The guiding tube is disposed on the clamping element. The spinal dynamic stabilization device passes through the guiding tube to arrive the adjacent vertebrae.

Note that the clamping apparatus further comprises a scale disposed adjacent to the clamping element to measure the expansion of the clamping element.

Note that the clamping apparatus further comprises an adjusting screw disposed on the handle element to control the expansion of the clamping element.

The invention provides a spinal dynamic stabilization device for decompression of narrowed spacing between adjacent vertebrae, foramen routes, for example, by increasing spacing of adjacent vertebrae. Each vertebra includes a sagittal plane. The spinal dynamic stabilization device includes at least a main body and a supporting member, and further includes a guiding and engaging mechanism for either open surgery or minimally invasive surgery procedures. The device enters a closed state and packed in the tube delivery tools. The closed device is guided and transported inside delivery tube, and then opened through designed mechanism once delivered at implant site. Note that the spinal dynamic stabilization device comprises a foldable supporting structure that can be stretched and lean against the spine. Foldable supporting structure is closed at the same direction of main body such as clam structure. The main body comprises a guiding groove. The foldable supporting structure comprises support portions, wherein the support portions pivot in relation to each other. The foldable supporting structure can also including, but not limiting to Opening of support elements can be achieved by certain mechanisms. For example, introduction of insertion part to trigger opening of foldable supporting structure. Firstly, the foldable supporting structure can be delivered to implant position, said interspinous process, and then followed by introducing insertion part. The pivoted support portions rotatably expand toward the adjacent vertebrae of the spine with control of insertion part which trigger opening of support structure. Whole system can be then positioned and stabilized between adjacent vertebrae. Delivery route can be parallel to either axial or saggital plane of spine. Support structure and insertion part further comprise slide bar and groove to guide conjugation of two elements and trigger opening of closed foldable supporting structure The spinal dynamic stabilization device spinal dynamic stabilization device further comprises at least a guiding element to guide the insertion part and the foldable supporting structure to move in the guiding tube.

Note that the main body and the foldable supporting structure are detachable.

Note that when the main body relatively moves away from the foldable supporting structure, the foldable supporting structure enters into a closed state, and when the main body relatively approaches the foldable supporting structure, the foldable supporting structure enters an open state.

Note that the main body further comprises a sensor, and the sensor is disposed on the main body for reacting to pressure.

Note that the main body further comprises a cone portion disposed on one end of the main body, and when the foldable supporting structure relatively approaches the main body, the cone portion props up the support portions.

Note that the support portions are U-shaped.
Note that the support portions are H-type.
Note that the support portions are foldable and H-type
Note that the support portions are claw-type.

Note that the foldable supporting structure is a unitary structure and a foldable structure.

Note that the foldable supporting structure further comprises a pivoting portion, and the support portions are pivoted via the pivoting portion and connect to the sliding bar.

Note that the sliding bar comprises an engaging portion, the engaging portion is disposed on one end of the sliding bar, and after the sliding enter the guiding groove, the main body is fixed via the engaging portion.

Note that the main body is an asymmetric column, especially cone structure located on at least one end.

Note that the main body is a column.

Note that the main body further comprises two depressions disposed on two sides of the main body.

Note that the main body and the foldable supporting structure are metal or nonmetal material.

Note that the main body and the foldable supporting structure are metal or nonmetal material coated with a flexible material, and the flexible material comprises macromolecular compounds or a flexible metal.

Note that the main body is made of a damping material.

Note that the main body is a fillable structure, and the main body is filled with a bone cement, a physiological solution or a flexible biological polymer material.

Note that the volume of the main body is changeable after being implanted or before being implanted.

Note that the shape of the main body is changeable after being implanted or before being implanted.

Note that the spinal dynamic stabilization device further comprises a shape memory alloy disposed between the support portions.

The invention provides a spinal dynamic stabilization device comprising a main body and a foldable supporting structure. When the main body enters the adjacent vertebrae, the foldable supporting structure expands toward the adjacent vertebrae of the spine.

Note that the spinal dynamic stabilization device further comprises a guiding element to provide the main body and the foldable supporting structure to move in the guiding tube.

Note that the spinal dynamic stabilization device further comprises a expanding mechanism, sliding bar wherein the foldable supporting structure comprises support portions, and when the sliding bar approaches the main body in the guiding element, the support portions expand toward the adjacent vertebrae of the spine and reaches a steady state to accomplish an implant procedure.

Note that the foldable supporting structure is fixed on the main body.

Note that the when the sliding bar relatively moves away from the main body, the support portions cover the main body.

Note that the support portions pivot in relation to each other.

Note that the sliding bar comprises a cone portion disposed on one end of the sliding bar, and when the sliding bar approaches the main body, the cone portion props up the support portions.

BRIEF DESCRIPTION OF DRAWINGS

The invention can be more fully understood by reading the subsequent detailed description and examples with references made to the accompanying drawings, wherein.

The invention can be more fully understood by reading the subsequent detailed description and examples with references made to the accompanying drawings.

DETAILED DESCRIPTION OF THE INVENTION

Figure 1:
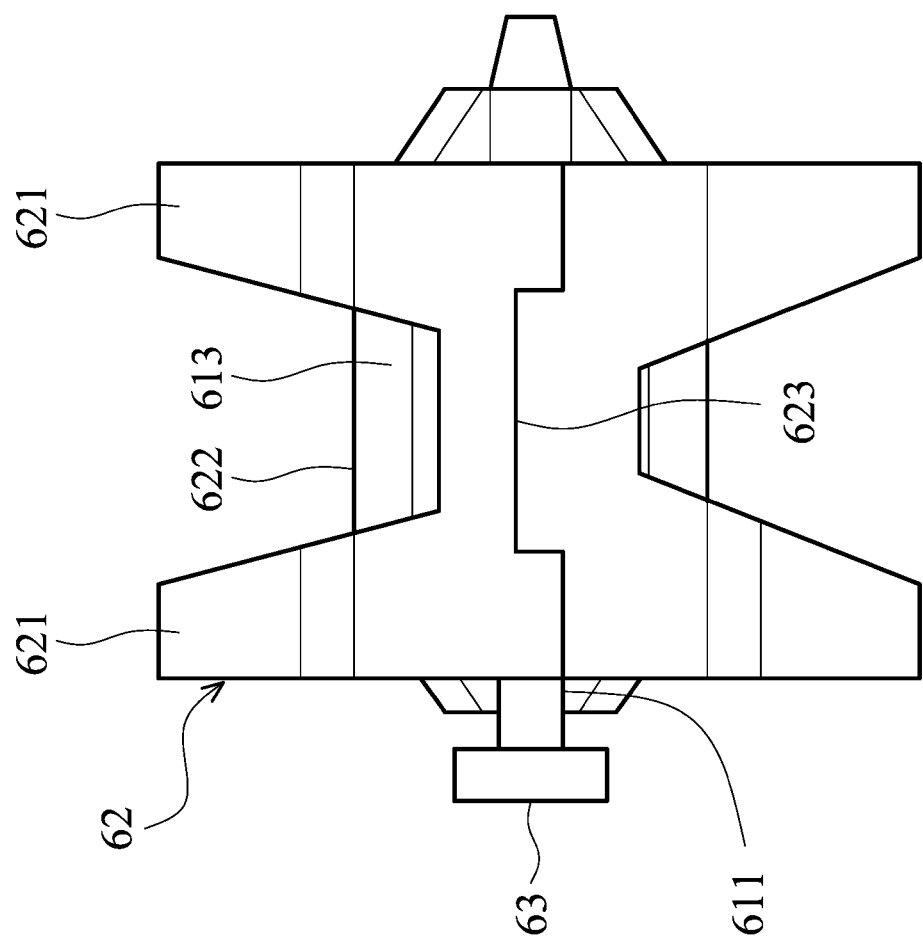
FIG. 1 is a schematic view showing a spinal dynamic stabilization device of the invention in an opened state.
Figure 10:
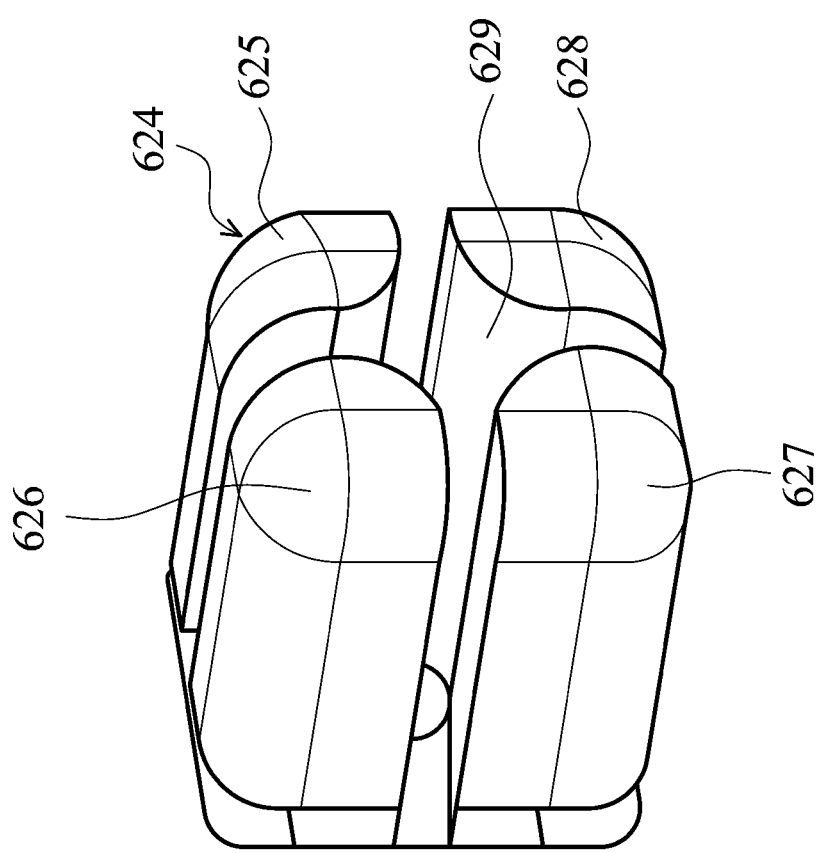
FIG. 10 is a schematic view showing an engaging portion of a spinal dynamic stabilization device of the invention.

FIG. 1 is a schematic view showing a spinal dynamic stabilization device of another embodiment of the invention. FIG. 10 is a schematic view showing an engaging portion of a spinal dynamic stabilization device of the invention.

Figure 4:
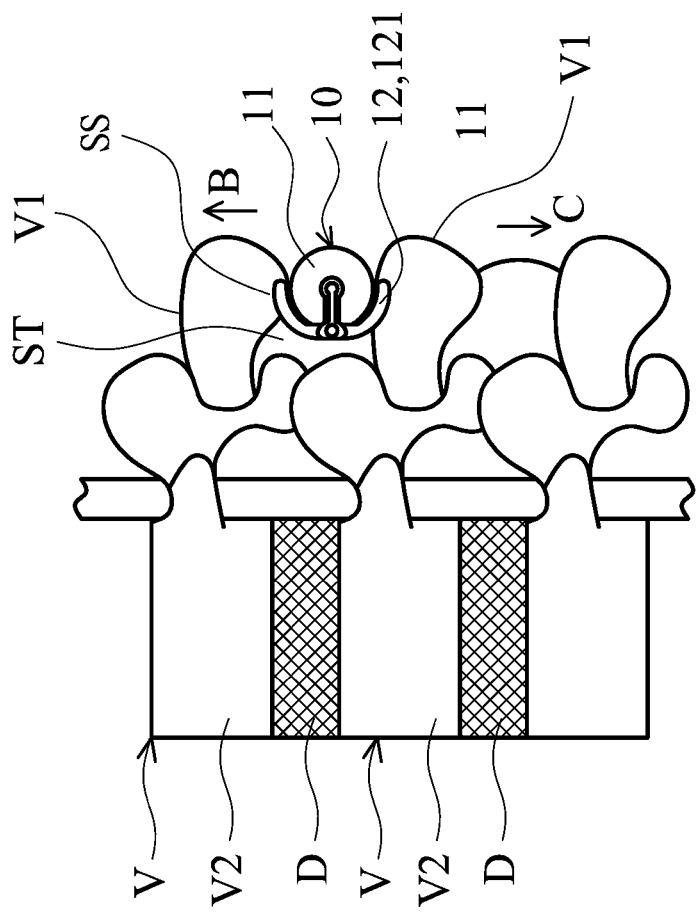
FIG. 4 is a schematic view showing a spinal dynamic stabilization device of the invention disposed between the adjacent vertebrae.

Referring to FIGS. 1, 4 and 10, the spinal dynamic stabilization device 60 comprises a main portion 61, two stabilizing portions 62 and an insertion portion 63. The main portion 61 comprises a guiding groove 611 for containing the insertion portion 63. Main portion 61 can further comprises a saddle portion 613 as the second load-bearing portion. The insertion portion 63 move in the guiding groove 611. Each stabilizing portion 62 comprises two arm portions 621 and 622. A pivot portion 623 is disposed between the stabilizing portions 62. Expanding of the stabilizing portions 62 can be actuated by either insertion of main portion 61 or insertion portion 63. When the main portion 61 or insertion portion 63 moves relatively toward stabilizing portion 62, the stabilizing portions 62 expand rotatably from posterior side of spine, on the right side of vertebrae in FIG. 4, toward the anterior side of spine, adjacent vertebrae V which shown on the left side of vertebrae in FIG. 4. The guiding groove 611, and the stabilizing portions 62 open pivotally away from the main portion 61 when the main portion 61 moves relative closer to the stabilizing portion 62. The expanding direction is defined from posterior side toward anterior side of spine. Plane of crossing area which generated by expanding of stabilizing portion is perpendicular to insertion direction of main portion 61. Note that stabilizing portion 622 provides a contact, or first load-bearing contact, between construct and upper vertebrae, or spinous process. Main portion 61 provides another contact, or secondary load-bearing portion, with spinous process. In some implementations, main portion 61 can further comprises a saddle portion 613 as the second load-bearing portion. Load distribution on spinal process can be redistributed by providing multiple contacts, first load-bearing and secondary load-bearing portion, in this example. Contact closer to anterior side of spine reduces tensile strength on vertebra when spine is extension. Distance between two opposite contacts at upper 622 and lower 622 is different from one generated between one between Main portion 61 and two adjacent processes. In some better implementations, anterior contact is higher than posterior contact. The former is used to provide first load-bearing site, and the latter is used to provide second load-bearing site to redistribute compressive loads. In this case, first load-bearing portion bears more loads than secondary load-bearing portion to reduce tensile strength occur at vertebrae, more particularly, pedicle area of spinal segment. The two stabilizing portion 62 that can move elastically or relatively by connected with elastic means, pivot portion, for example. The stabilizing portion 62 can also be comprised of flexible, damping materials or with those materials coated. Those contacts on anterior portion of device can move relatively that result from damping property of device.

Note that the insertion portion 63 comprises an engaging portion 624 with four portions 625, 626, 627 and 628 in FIG. 10. One end of the portions 625, 626, 627 and 628 are connected to each other. The portions 625, 626, 627 and 628 are arranged to generate a gap 629 therebetween. When the engaging portion 624 in the guiding groove 611, the portions 625, 626, 627 and 628 are compressed closely. After the engaging portion 624 passes through the guiding groove 611, the portions 625, 626, 627 and 628 are released to prop the guiding groove 611, thus, the stabilizing portions 62 is stably inserted in the guiding groove 611. In this embodiment, the stabilizing portion may be U, or H shaped. The stabilizing structure 62 is a unitary member and a foldable structure and when the stabilizing structure 62 is hidden in or connected to main portion 61 as train-like construct, wherein the stabilizing structure 62 is in a closed state. In other embodiments, the main portion 61 may be an asymmetric column, or with cone-like shape on the one end and connecting portion to connect instrument at distal end. For surgery, device can be delivered from unilateral of spinal process to minimize injury of other tissues, muscle, for example.

Figure 2:
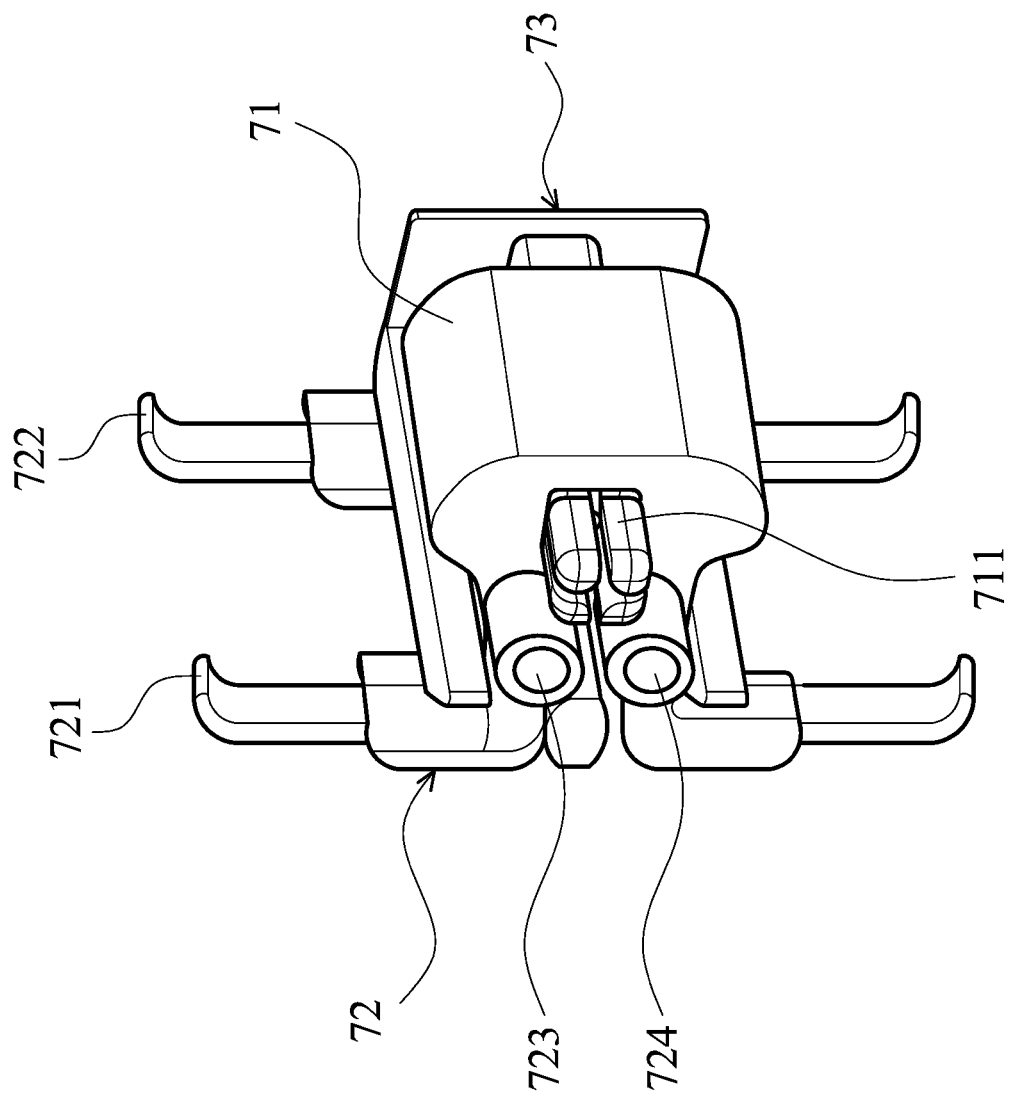
FIG. 2 is a schematic view showing a spinal dynamic stabilization device of another embodiment of the invention.

FIG. 2 is a schematic view showing a spinal dynamic stabilization device of another embodiment of the invention.

Referring to FIG. 2, the spinal dynamic stabilization device 70 comprises a main portion 71, two stabilizing portions 72 and an insertion portion 73. The main portion 71 comprises a guiding groove 711 for containing the insertion portion 73. The insertion portion 73 move in the guiding groove 711. Each stabilizing portion 72 comprises two arm portions 721 and 722. Two pivot portions 723 and 724 are disposed on the main portion 71 to respectively connect to the stabilizing portions 72. The stabilizing portions 72 are pivoted on the main portion 71. When the insertion portion 73 moves in the guiding groove 611 relatively to main portion 71, the stabilizing portions 72 expand rotatably toward the sagittal plane V1. Note that the arm portions 721 and 722 are telescopic.

Figure 3:
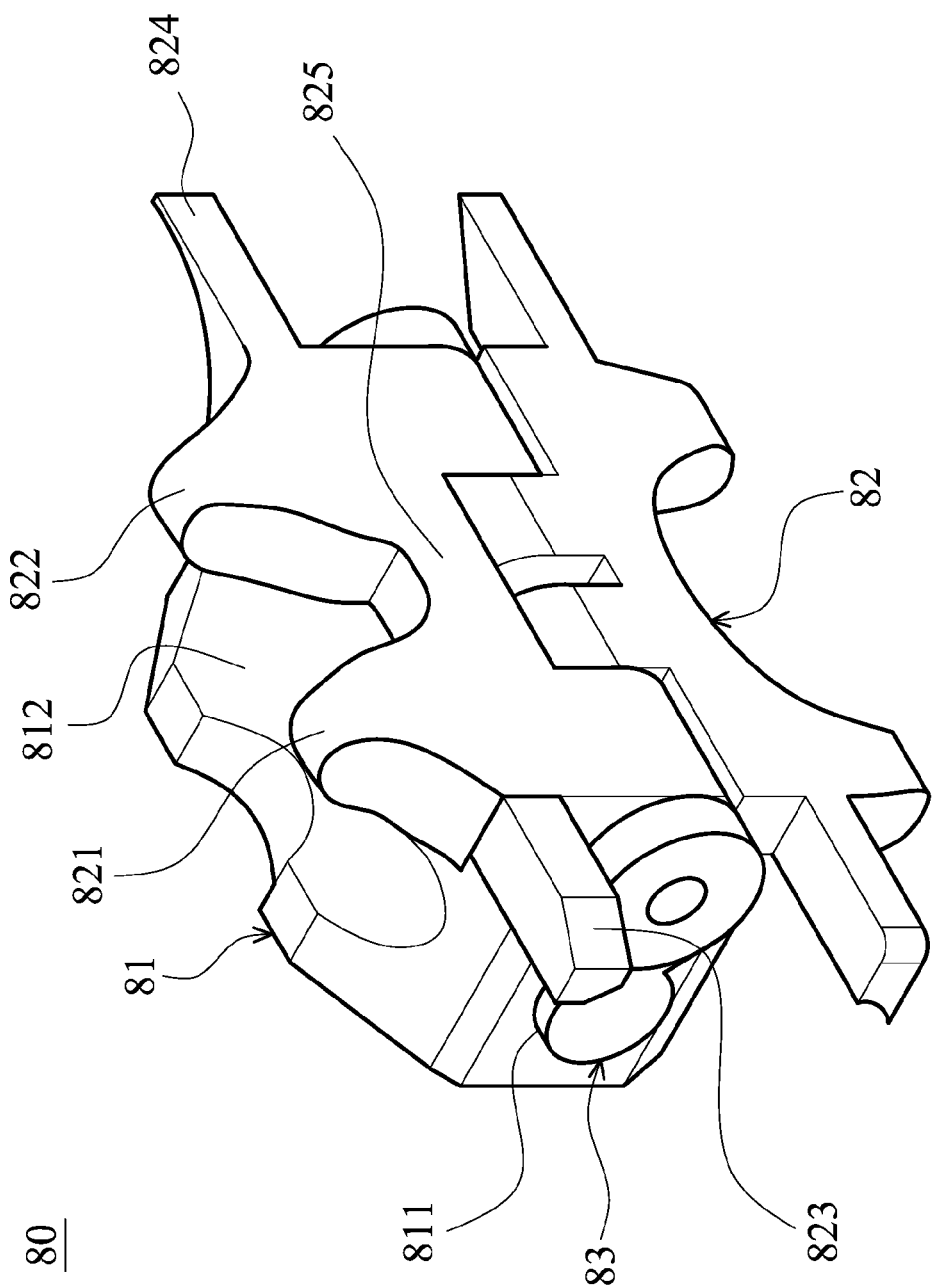
FIG. 3 is an schematic view showing a spinal dynamic stabilization device of another embodiment of the invention.

FIG. 3 is a schematic view showing a spinal dynamic stabilization device of another embodiment of the invention.

Referring to FIG. 3, a spinal dynamic stabilization device 80 comprises a main portion 81, a foldable stabilizing structure 82, and an insertion portion 83. The main portion 81 comprises a guiding groove 811 and a depression 812. The guiding groove 811 contains the insertion portion 83. The stabilizing structure 82 comprises two arm portions 821 and 822, two lateral protrusion 823 and 824, and a connecting portion 825 between the arm portions 821 and 822. The protrusion can be located either on stabilizing portion 82 or main portion 81. In some better implementations. The length of opened device can be ranged from 10 mm to 50 mm to fit different shape of vertebra segments, more particularly, the vacancy between adjacent laminar portion. The insertion portion 811 movably connects to the main portion 81. When the stabilizing portion 82 covers the main portion 81 (shown in FIG. 12), the depression 812 is higher than the connecting portion 825. Referring to FIG. 4, when implanting the spinal dynamic stabilization device 80, the spinal process SS is supported by two saddle portions on stabilizing portion 82 and main portion 81 respectively. First saddle portion located between arm portions 821 and 822 and second saddle portion disposed on main portion 81. On some applications, first saddle portion is higher than second one to bear more compression loads.

FIG. 4 is a schematic view showing a spinal dynamic stabilization device of the invention disposed between the adjacent vertebrae.

Referring to FIGS. 1 to 4, the spinal dynamic stabilization device 10 of the invention is implanted between two adjacent vertebrae V to relief pain by alternating size of spinal canal or foramen between the adjacent vertebrae V. The adjacent vertebrae V comprise a sagittal plane V1, a vertebra body V2, a soft tissue ST and a spinal process SS. The intervertebral disk D is disposed between the adjacent vertebrae body V2. The soft tissue ST is disposed between the adjacent sagittal plane V1.

Figure 5:
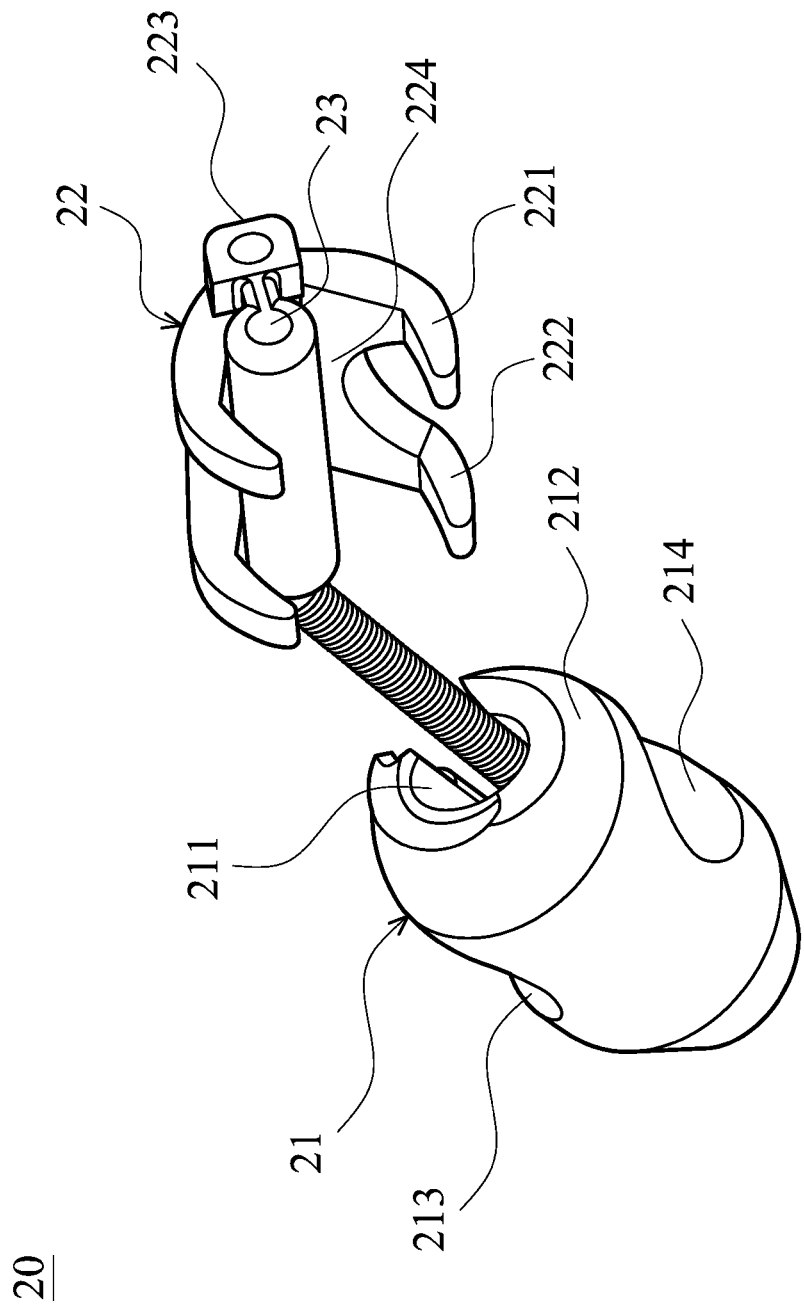
FIG. 5 is a schematic view showing a spinal dynamic stabilization device of another embodiment of the invention.
Figure 6:
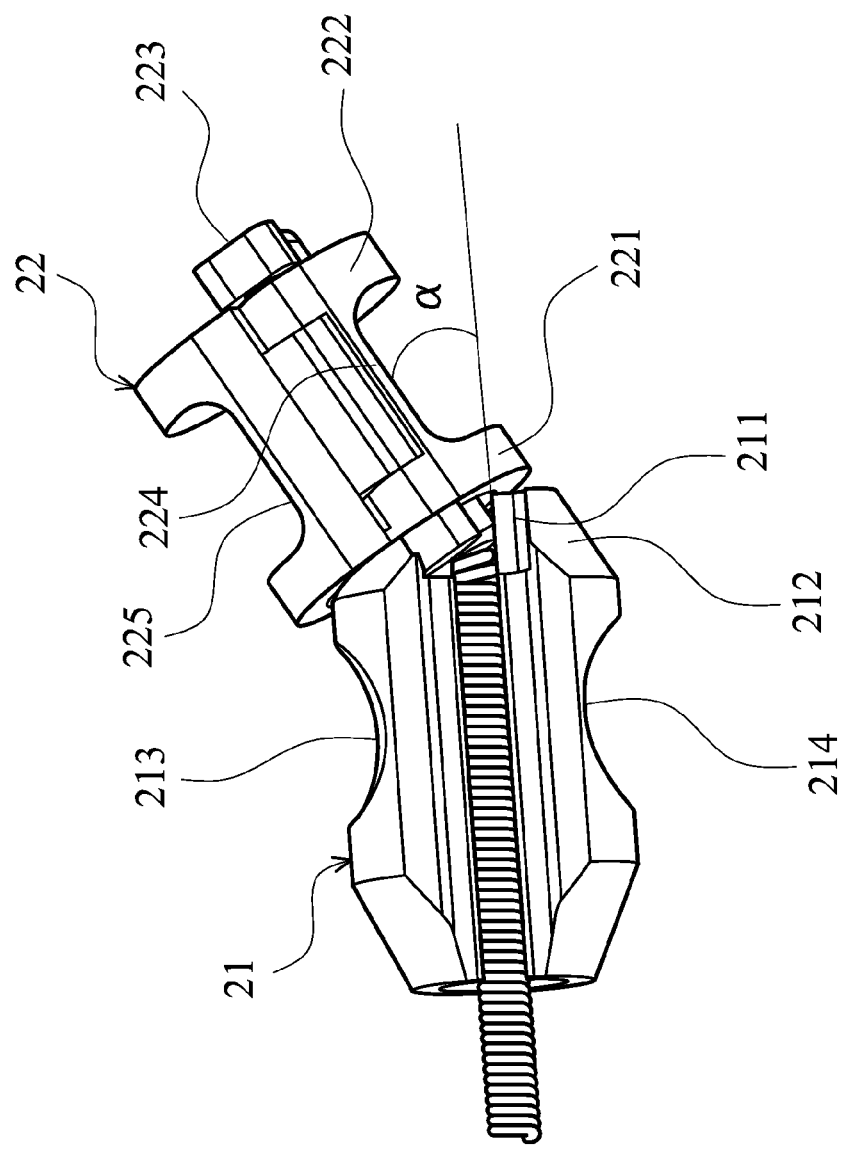
FIG. 6 is a schematic view showing a spinal dynamic stabilization device of another embodiment of the invention in a closed state.
Figure 7:
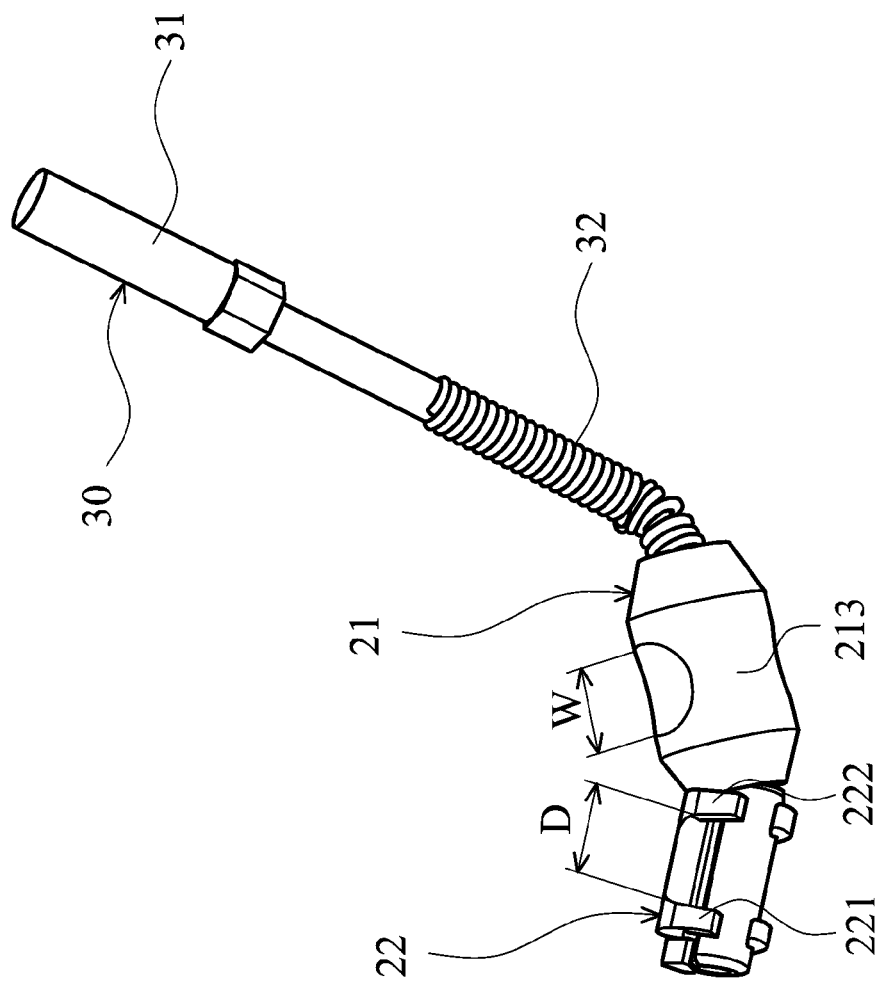
FIG. 7 is a schematic view showing a spinal dynamic stabilization device with a guiding element of another embodiment of the invention.

FIG. 5 is an exploded view showing a spinal dynamic stabilization device of another embodiment of the invention. FIG. 6 is a schematic view showing a spinal dynamic stabilization device of another embodiment of the invention in a closed state with curvature which minimizes damage of soft tissue during installation. In addition, non-linear construct of device shorten path of device transportation inside body. FIG. 7 is a schematic view showing a spinal dynamic stabilization device with a guiding element of another embodiment of the invention.

Referring to FIGS. 5 to 7, a spinal dynamic stabilization device 20 comprises a main portion 21, a foldable stabilizing structure 22, and an insertion portion 23. The main portion 21 comprises a guiding groove 211 to contain the insertion portion 23. The foldable stabilizing structure 22 comprises two arm portions 221 and 222 and a connecting portion 224 between the arm portions 221 and 222, and is detachably installed on the main portion 21 (shown in FIGS. 5 and 6). The arm portion 221 comprises a saddle portion 225 to provide a contact as first load bearing portion. The main portion comprises depressions 213 as secondary load-bearing portion. In some implementation, saddle portion 225 is higher than depressions 213. The arm portions 221 and 222 are pivoted in relation to each other. The insertion portion 23 connects to the stabilizing structure 22 and the main portion 21. The spinal dynamic stabilization device 20 further comprises a guiding element 30 for pushing the main portion 21, the foldable stabilizing structure 22 and the insertion portion 23. The guiding element 30 comprises a handle portion 31 and a flexible portion 32. The flexible portion 32 can be connected to stabilizing structure 22 or insertion portion 23 that gives flexibility between stabilizing structure 22 and man body 21 before device installation. The handle portion 31 provides a user for holding and the flexible portion 32 is connected to the main portion 21 for installation of device along curved path.

When the main portion 21 enters the adjacent vertebrae V (shown in FIG. 4), the foldable stabilizing structure 21 rotatably opens toward vertebrae V of the spine of the patient. When the main portion 21 relatively moves away from the stabilizing structure 22, the stabilizing structure is at a closed state, and an included angle α is formed between the stabilizing structure 22 and the main portion 21 to facilitate delivery of device from unilateral side of spinal process. Thus, when implanting the spinal dynamic stabilization device 20, the stabilizing structure 22 and the main portion 21 have the included angle α for precise installation to the site that as closer to laminar site as possible.

The main portion 21 comprises a cone portion 212 disposed on one end of main portion 21. When the main portion 21 is pushed to approach the stabilizing structure 22, the arm portions 221 and 222 open. As a result, the cone portion 212 smoothly props up the arm portions 221 and 222, as shown in FIG. 6. Note that the main portion 21 comprises depressions 213 and 214 disposed on sides of the main portion 21 for decreasing pressure on the soft tissue ST (shown in FIG. 4). When the stabilizing portion 22 covers the main portion 11, the depressions 213 and 214 are higher than the connecting portion 224. An interval distance D between the arm portions 221 and 222 of the stabilizing portion 22 is larger than the width W of the depression 213. Referring to FIG. 4, when implanting the spinal dynamic stabilization device 20, the spinal process SS is supported by the depressions 213 and 214, and the arm portions 221 and 222 clip or hold the side of the spinal processes SS. The insertion portion 23 comprises a pivot portion 223, and the pivot portion 223 is disposed on one end of the insertion portion 23 to rotatably connect to the stabilizing portions 22. Note that the main portion 21 and the stabilizing structure 22 are made of metal or nonmetal. The main portion 21 and the stabilizing structure 22 are metal or nonmetal material coated with a flexible material, and the flexible material comprises macromolecular compounds or a flexible metal.

In this embodiment, the arm portions may be a clam-type, U-type or H-type arm portion. The stabilizing structure 22 is a unitary member and a foldable structure and when the main portion 21 is pushed toward the stabilizing structure 22, the stabilizing structure 22 opens.

Figure 8:
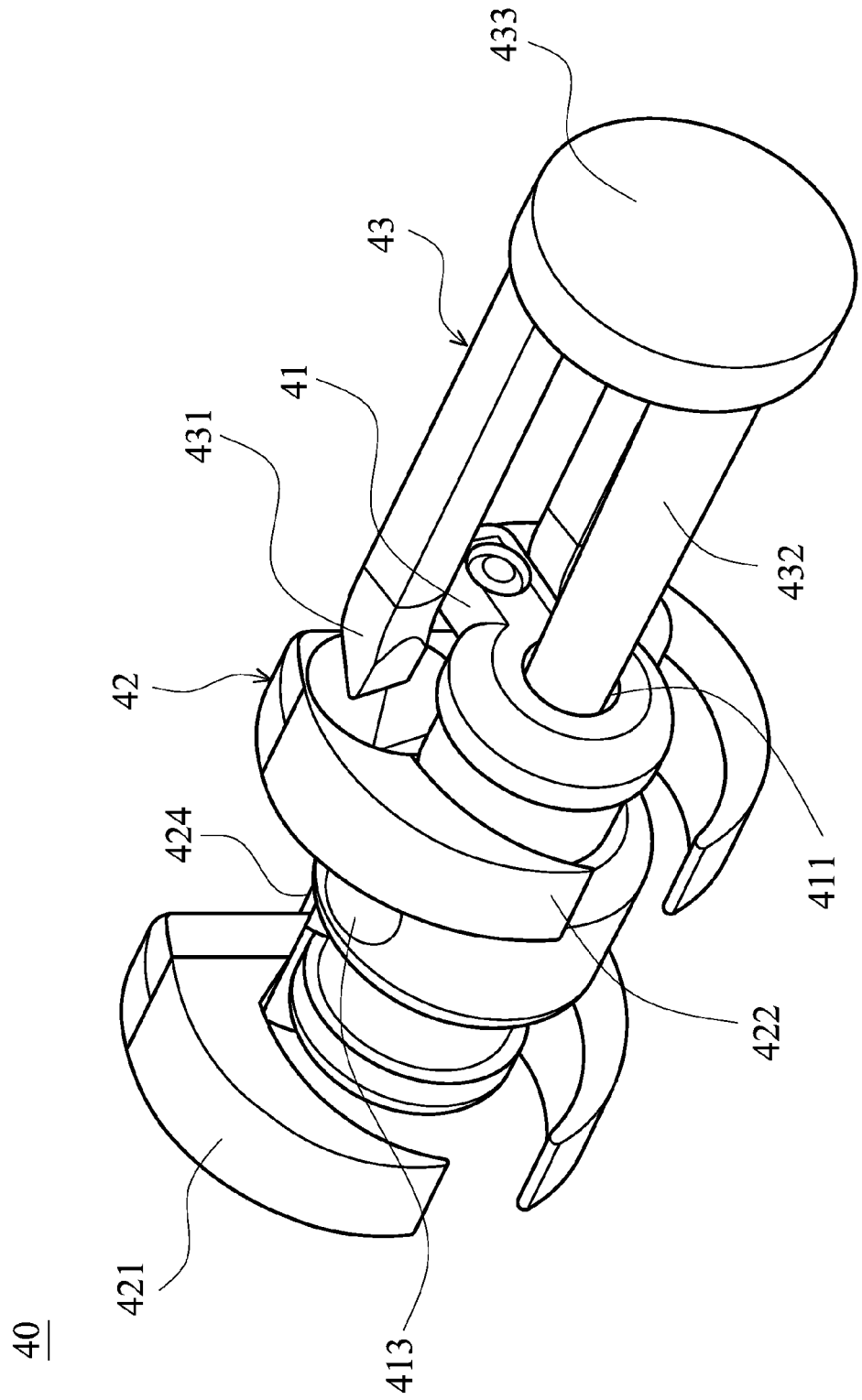
FIG. 8 is a schematic view showing a spinal dynamic stabilization device of another embodiment of the invention in a closed state.
Figure 9:
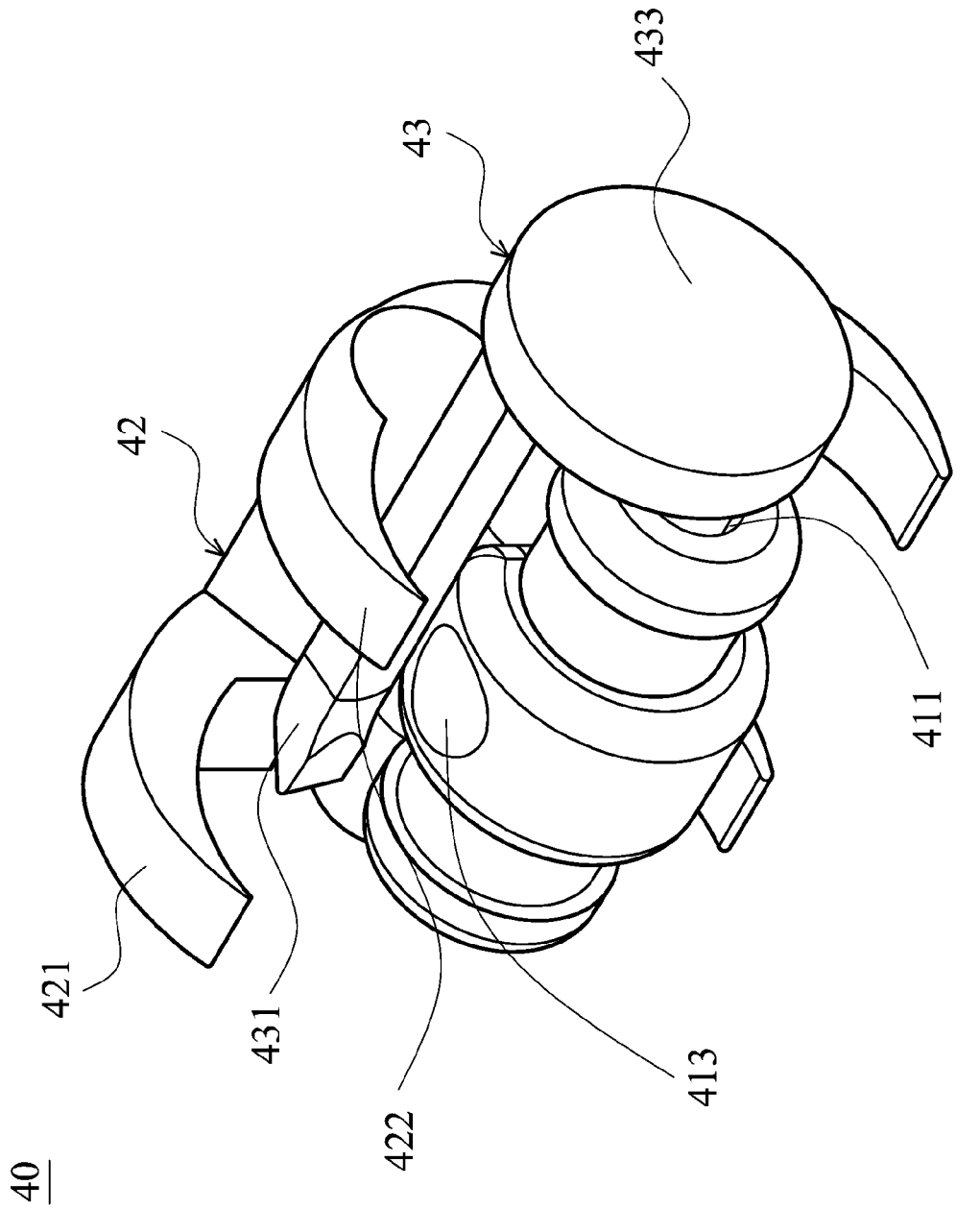
FIG. 9 is a schematic view showing a spinal dynamic stabilization device of another embodiment of the invention in an opened state.

FIG. 8 is a schematic view showing a spinal dynamic stabilization device of another embodiment of the invention in a closed state. FIG. 9 is a schematic view showing a spinal dynamic stabilization device of another embodiment of the invention in an opened state.

The insertion portion 43 is in a pin-like shape, and the insertion portion 43 comprises three sliding portions 432 and a pushing portion 433. At least one of the sliding portions 432 comprises a cone angle 431. The pushing portion 433 connects to the sliding portions 432. When the pushing portion 433 is exerted by a force, one of the sliding portions 432 inserts into the guiding groove 411 and the stabilizing structure 42 expand. Note that the main portion 41 comprises a depression 413. The stabilizing structure 42 comprises two arm portions 421 and 422, and a connecting portion 424. When the stabilizing portion 42 opened, the depression 413 is lower than the connecting portion 424 to redistribute compression loads. Opening direction as similar to one that described in FIG. 1. Thus, shown in FIG. 4, when implanting the spinal dynamic stabilization device 40, the spinal process SS is supported by the depression 413 and connecting portion 424. Connecting portion 424 bearing more compression loads than depression 413 to redistribute loads. The arm portions 421 and 422 hold or clip the side of the spinal processes SS.

Figure 11:
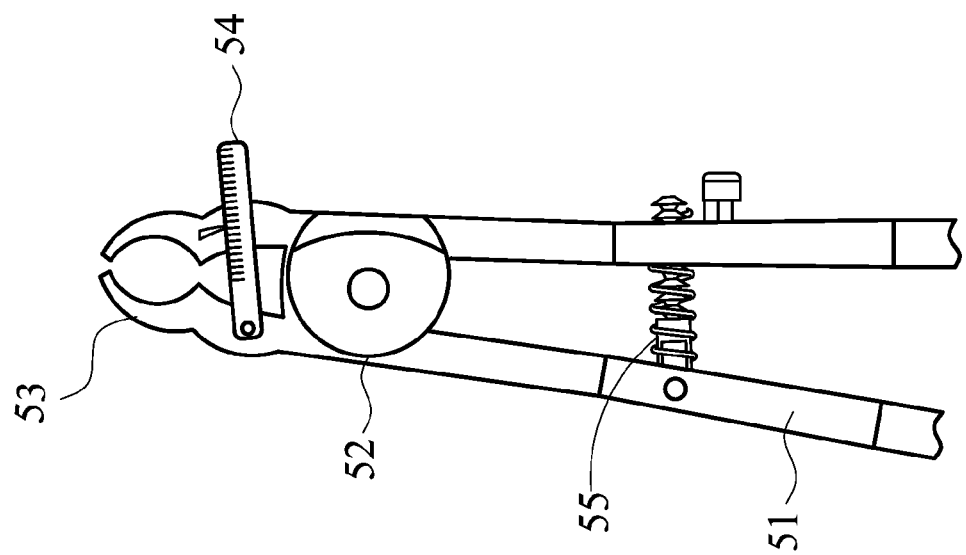
FIG. 11 is a schematic view showing a clamping apparatus of the invention.
Figure 12:
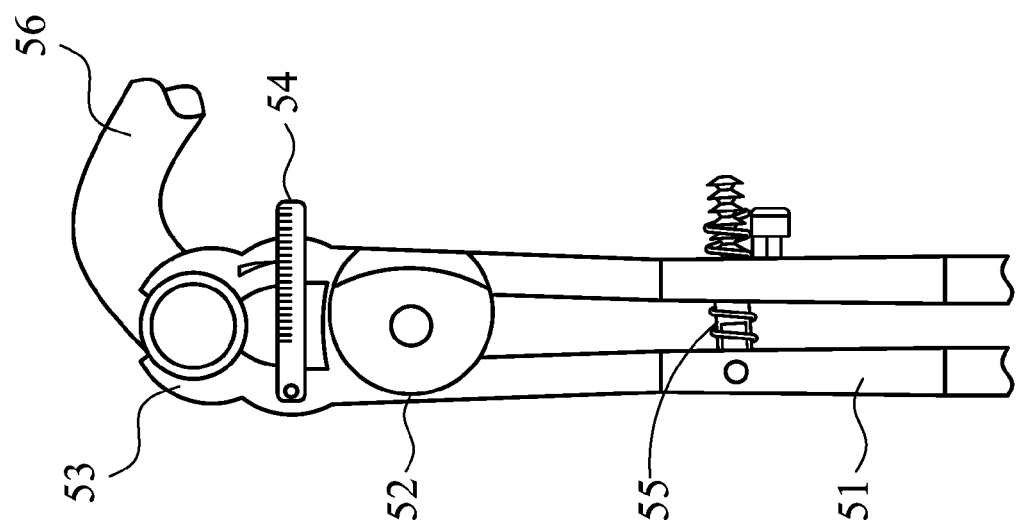
FIG. 12 is another schematic view showing a clamping apparatus of the invention.

FIG. 11 is a schematic view showing a clamping apparatus of the invention. FIG. 12 is another schematic view showing a clamping apparatus of the invention.

The clamping apparatus 50 holds a spinal dynamic stabilization device 10 (shown in FIG. 4) to adjacent vertebrae V. The clamping apparatus 50 comprises a handle element 51, a clamping element 53, a connecting member 52 and a guiding tube 56. The handle element 51 and the clamping element 53 are connected by the connecting member 52. The guiding tube 56 is disposed on the clamping element 53. The spinal dynamic stabilization device 10 (shown in FIG. 4) passes through the guiding tube 56 to arrive the adjacent vertebrae V (shown in FIG. 4). The clamping apparatus 50 further comprises a scale 54 disposed adjacent to the clamping element 53 to measure the expansion of the clamping element 53. The clamping apparatus 50 further comprises an adjusting screw 55 disposed on the handle element 51 to control the expansion of the clamping element 53.

Figure 13:
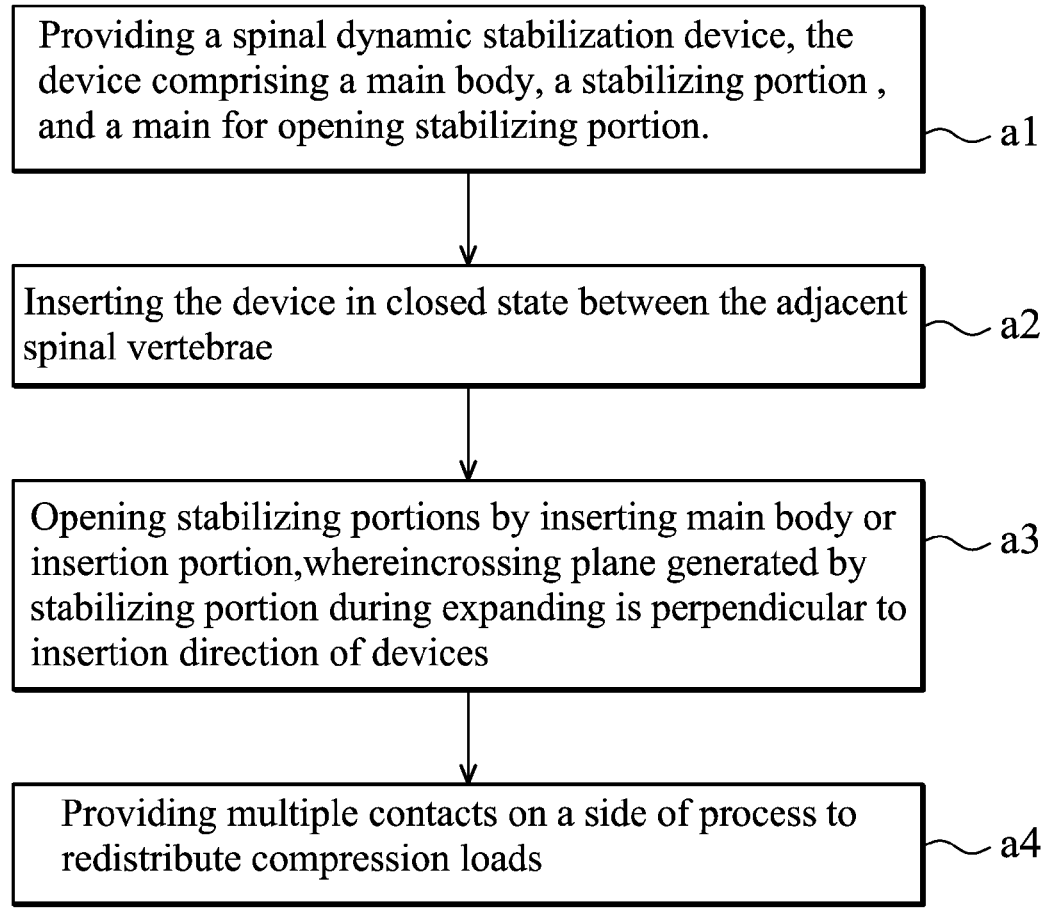
FIG. 13 is a flow chart of a surgical method for distracting adjacent spinal vertebrae of the invention.

FIG. 13 is a flow chart of a surgical method for distracting adjacent spinal vertebrae of the invention.

Referring to FIGS. 1, 4, 5, 6 and 13, each spinal vertebrae comprises a spinal process SS. The steps comprise: a1. providing a spinal dynamic stabilization device, the spinal dynamic stabilization device 20 comprising a main portion 21 with a depression 213, a stabilizing portion 22 with two arm portions 221 and 222 and a connecting portion 224 between the arm portions 221 and 222, pivoting on the main portion 21, and an insertion portion 23 movably connecting to the main portion 21, wherein when the stabilizing portion 22 covers the main portion 21, the distance between depressions 213 and 214 is different from one between two saddle portion of stabilizing portion 22.; a2. Inserting the spinal dynamic stabilization device 20 in a closed state between the adjacent spinal vertebrae V; a3. Opening stabilizing portions 22 by inserting main portion 21 or insertion portion 63 (shown in FIG. 1), wherein crossing plane generated by stabilizing portion during expanding is perpendicular to insertion direction of devices; a4. Providing multiple contacts between device and adjacent processes, contacts on the main portion 21 and stabilizing portion 22, on a side of process to redistribute compression loads.

Figure 14:
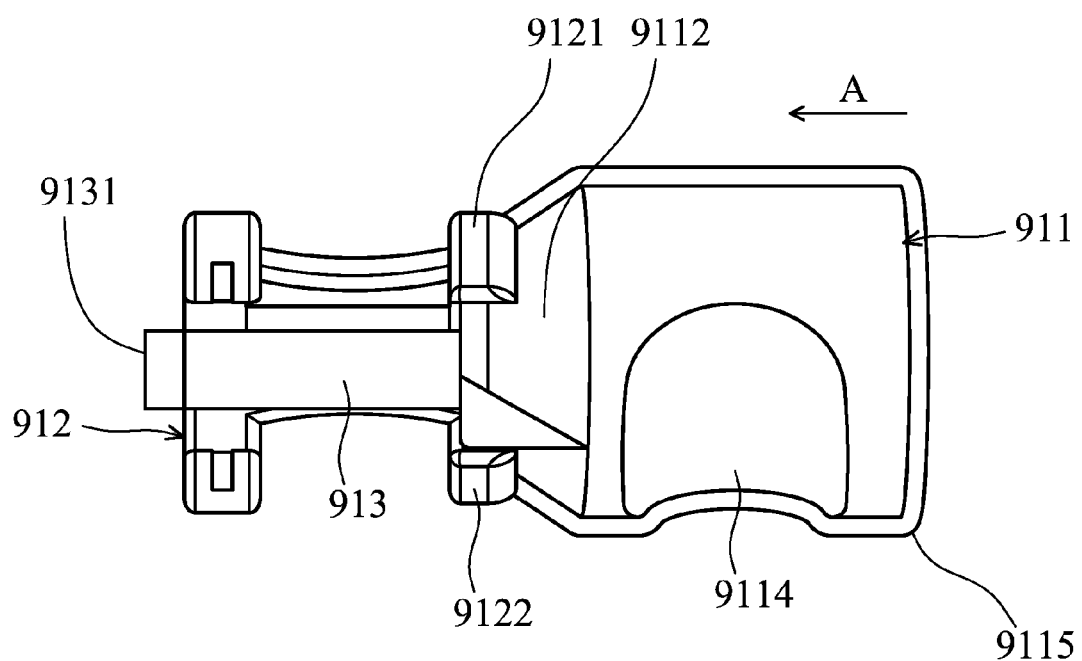
FIG. 14 is a schematic view showing a spinal dynamic stabilization device of the invention in a closed state.
Figure 15:
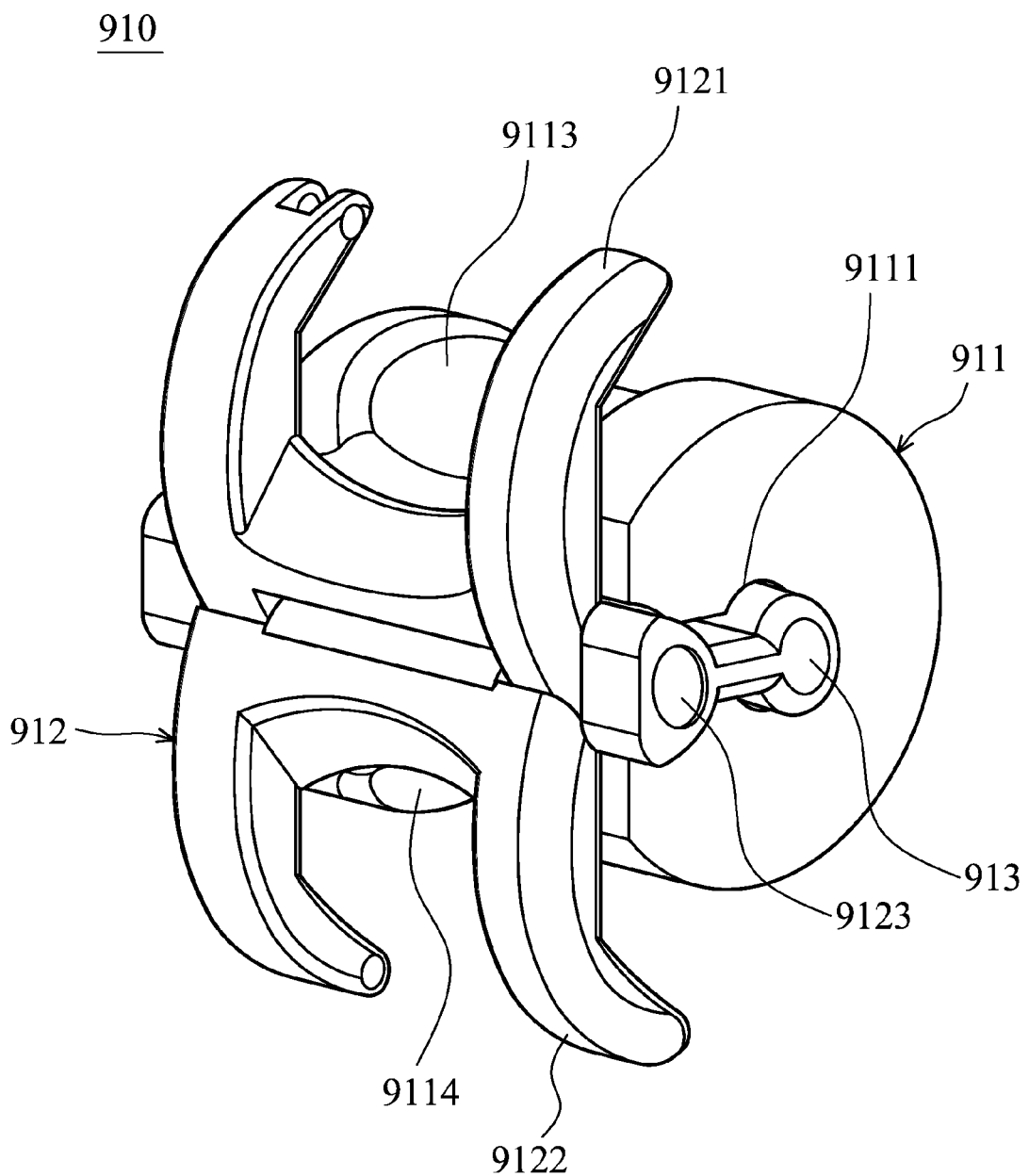
FIG. 15 is a schematic view showing a spinal dynamic stabilization device of the invention in an opened state.

FIG. 14 is a schematic view showing a spinal dynamic stabilization device of the invention in a closed state. FIG. 15 is a schematic view showing a spinal dynamic stabilization device of the invention in an opened state.

Referring to FIGS. 14 and 15, a spinal dynamic stabilization device 910 comprises a main portion 911, a foldable stabilizing portion 912 and a sliding bar 913. The main portion 911 comprises a guiding groove 9111, a cone portion 9112 and two depressions 9113 and 9114. The cone portion 9112 is disposed on one end of the main portion 911. The depressions 9113 and 9114 are disposed on the upper side and a lower side of the main portion 911. The foldable stabilizing portion 912 comprises two arm portions 9121 and 9122, and a pivoting portion 9123. The arm portions 9121 and 9122 are pivoted in relation to each other. The sliding bar 913 comprises an engaging portion 9131 disposed on one end of the sliding bar 913. The sliding bar 913 is connected to the pivoting portion 9123 of the foldable stabilizing portion 912 and movable in the guiding groove 9111.

In this embodiment, the arm portions may be a clam-type, U-type or H-type arm portions. The foldable stabilizing portion 912 is a unitary member and a foldable structure. The clam of the arm portions 9121 and 9122 are curved toward the main portion 911. When the main portion 911 is at an appropriate distance away from the foldable stabilizing portion 912, the foldable stabilizing portion 912 enters a closed state, as shown in FIG. 14. When the main portion 911 approaches the foldable stabilizing portion 912, the foldable stabilizing portion 912 is propped, as shown in FIG. 15. The main portion 911 further comprises flexible polymer material 9115 to cover the main portion 911. The main portion 911 may be an asymmetric column. The main portion 911 and the foldable stabilizing portion 912 are made of metal or nonmetal. The main portion 911 is a hollow structure, and the main portion 911 is filled with a bone cement, a physiological solution or a flexible biological polymer material.

Figure 16:
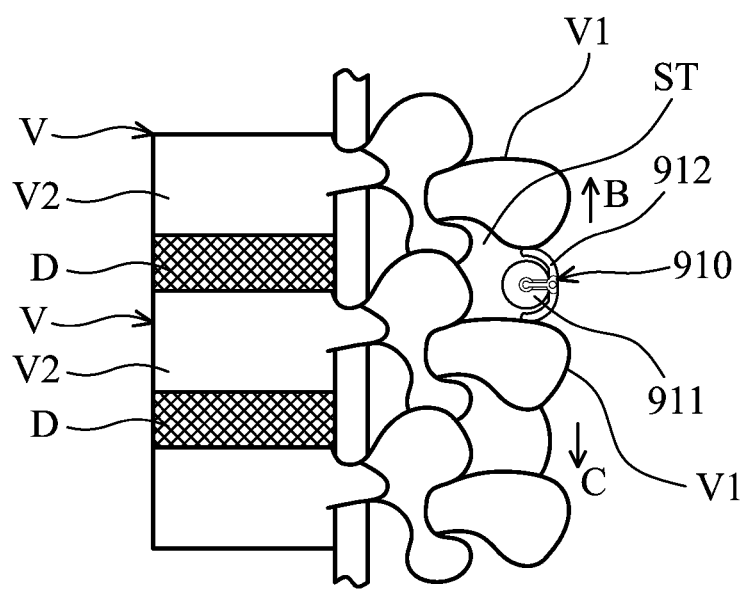
FIG. 16 is a schematic view showing a spinal dynamic stabilization device of the invention disposed between the adjacent vertebrae.

FIG. 16 is a schematic view showing a spinal dynamic stabilization device of the invention disposed between the adjacent vertebrae.

Referring to FIGS. 14 to 16, when the interval between the adjacent vertebrae V decreases, the spinal dynamic stabilization device 910 of the invention is implanted between the adjacent vertebrae V. The adjacent vertebrae V comprise a sagittal plane V1, a vertebra body V2 and a soft tissue ST. The intervertebral disk D is disposed between the adjacent vertebrae body V2. The soft tissue ST is disposed between adjacent sagittal plane V1.

Using minimally invasive surgery (or MIS), the spinal dynamic stabilization device 910 with the foldable stabilizing portion 912 in the closed state is installed in a endoscopic tube, and is pushed to the soft tissue ST between the adjacent sagittal plane V1 via tools. The main portion 911 is pushed along an arrow A. When the main portion advances, the sliding bar 913 moves in the guiding groove 9111 to provide the main portion 911 to approach the foldable stabilizing portion 912. The cone angle 9112 helps the main portion 911 to stably approach the foldable stabilizing portion 912. Thus, the arm portions 9121 and 9122 are expanded smoothly. After expanding the arm portions 9121 and 9122, that is, the main portion 911 approaches the foldable stabilizing portion 912, the foldable stabilizing portion 912 is propped up (as shown in FIGS. 15 and 16). The arm portions 9121 and 9122 are rotatably expanded toward the sagittal plane V1 of the adjacent vertebrae V (along arrows B and C).

Note that the sliding bar 913 of the spinal dynamic stabilization device 910 comprises an engaging portion 9131 disposed on one end of the sliding bar 913. When the sliding bar 913 completely enters the guiding groove 9111, the main portion 911 is fixed via the engaging portion 9131 because of the engaging portion 9131 is greater in width than the guiding groove 9111. Installation of the depressions 9113 and 9114 decrease pressure on the soft tissue ST.

The spinal dynamic stabilization device 910 of the invention is applied to MIS procedures. When the spinal dynamic stabilization device 910 is implanted into the adjacent vertebrae V, the foldable stabilizing portion 912 is held in a closed state. When the spinal dynamic stabilization device 910 reaches the adjacent vertebrae V that are required to be propped, the main portion 911 is pushed to close the foldable stabilizing portion 912. At this time, the arm portions 9121 and 9122 of the foldable stabilizing portion expand to stretch toward the sagittal plane V1 of the adjacent vertebrae V. Thus, only a small incision is inflicted when implanting the spinal dynamic stabilization device 910 of the invention, decreasing blood lost and complications for a speedier recovery.

Meanwhile, the spinal dynamic stabilization device 910 can be restored, so that a normal physiological interval between the adjacent vertebrae V is kept.

Figure 17A:
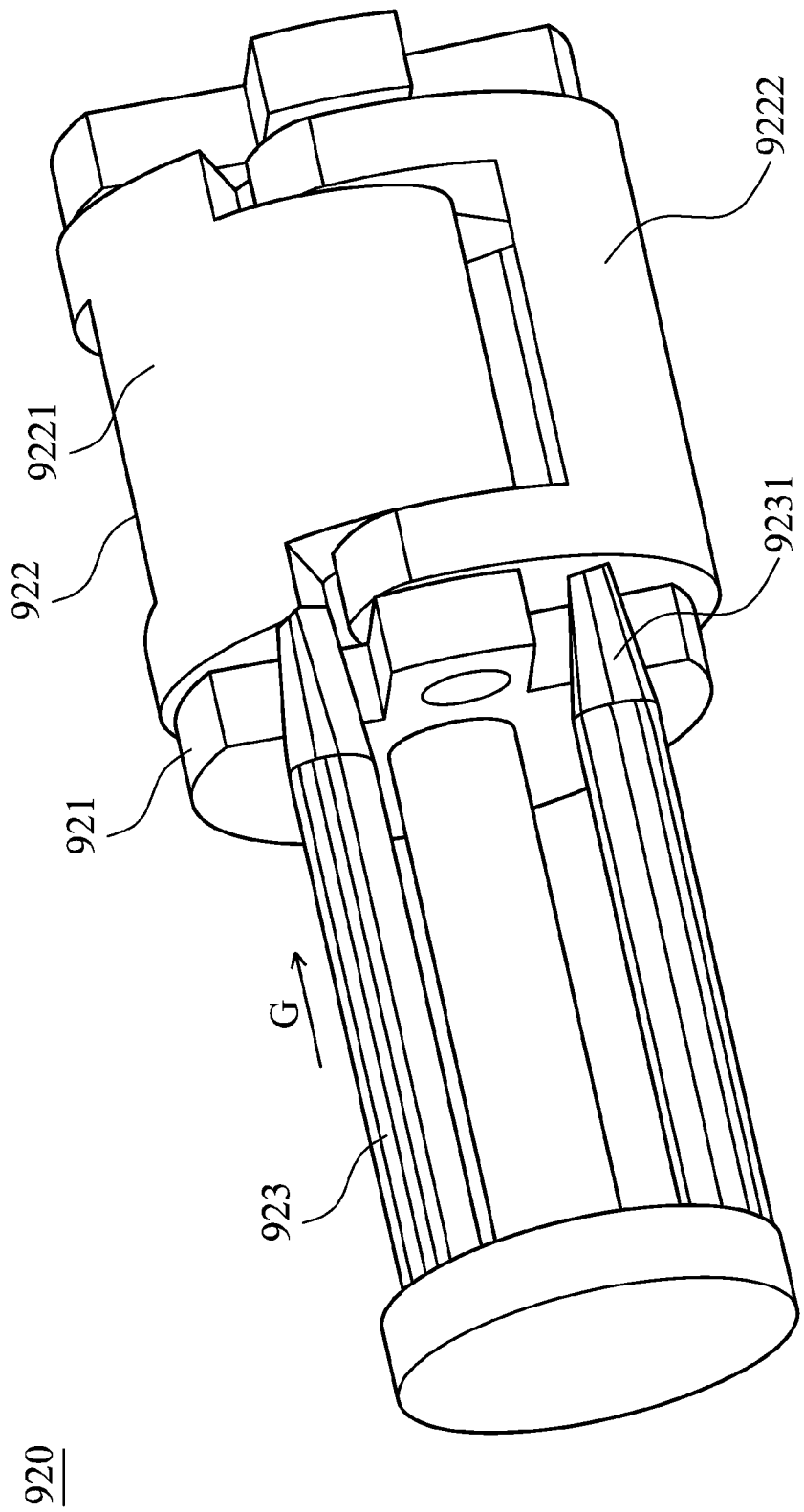
FIG. 17A is a schematic view showing a main portion relatively moving away from a foldable supporting structure of another embodiment of a spinal dynamic stabilization device of the invention.
Figure 17B:
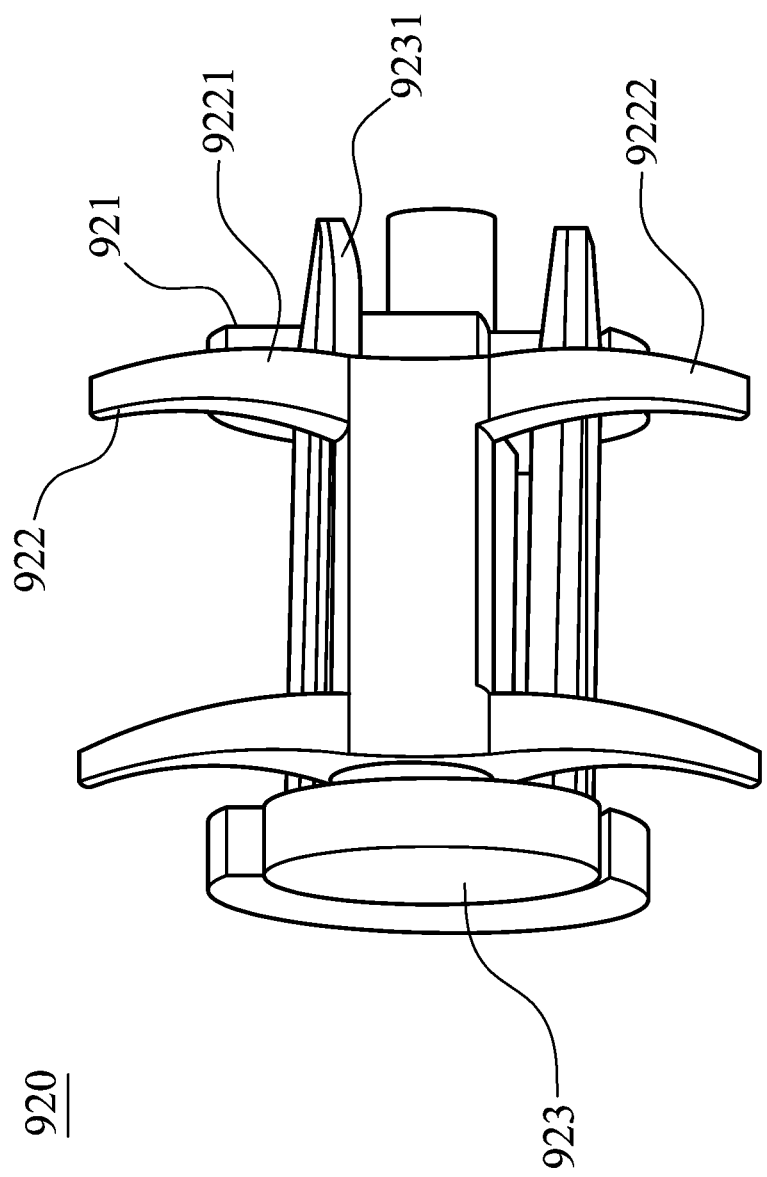
FIG. 17B is a schematic view showing a main portion relatively approaching a foldable supporting structure of another embodiment of a spinal dynamic stabilization device of the invention.

FIG. 17A is a schematic view showing a main portion relatively moving away from a foldable stabilizing portion of another embodiment of a spinal dynamic stabilization device of the invention. FIG. 17B is a schematic view showing a main portion relatively approaching a foldable stabilizing portion of another embodiment of a spinal dynamic stabilization device of the invention.

Referring to FIGS. 17A and 17B, a spinal dynamic stabilization device 920 comprises a main portion 921, a foldable stabilizing portion 922 and a sliding bar 923. The foldable stabilizing portion 922 comprises two arm portions 9221 and 9222 and is installed on the main portion 921. The arm portions 9221 and 9222 are pivoted in relation to each other. The sliding bar 923 is installed movably between the main portion and the foldable stabilizing portion 922. The sliding bar 923 comprises a cone angle 231 disposed on one end closer the main portion 921 (shown in FIGS. 17A and 17B). When the sliding bar 923 relatively moves away from the main portion 921, the arm portions 9221 and 9222 cover the main portion 921. When the main portion 921 enters between the adjacent vertebrae V (shown in FIG. 3), the sliding bar 923 is pushed to approach the main portion 921 along an arrow G. As a result, the arm portions 9221 and 9222 are propped up smoothly, as shown in FIGS. 17A and 17B.

Figure 18A:
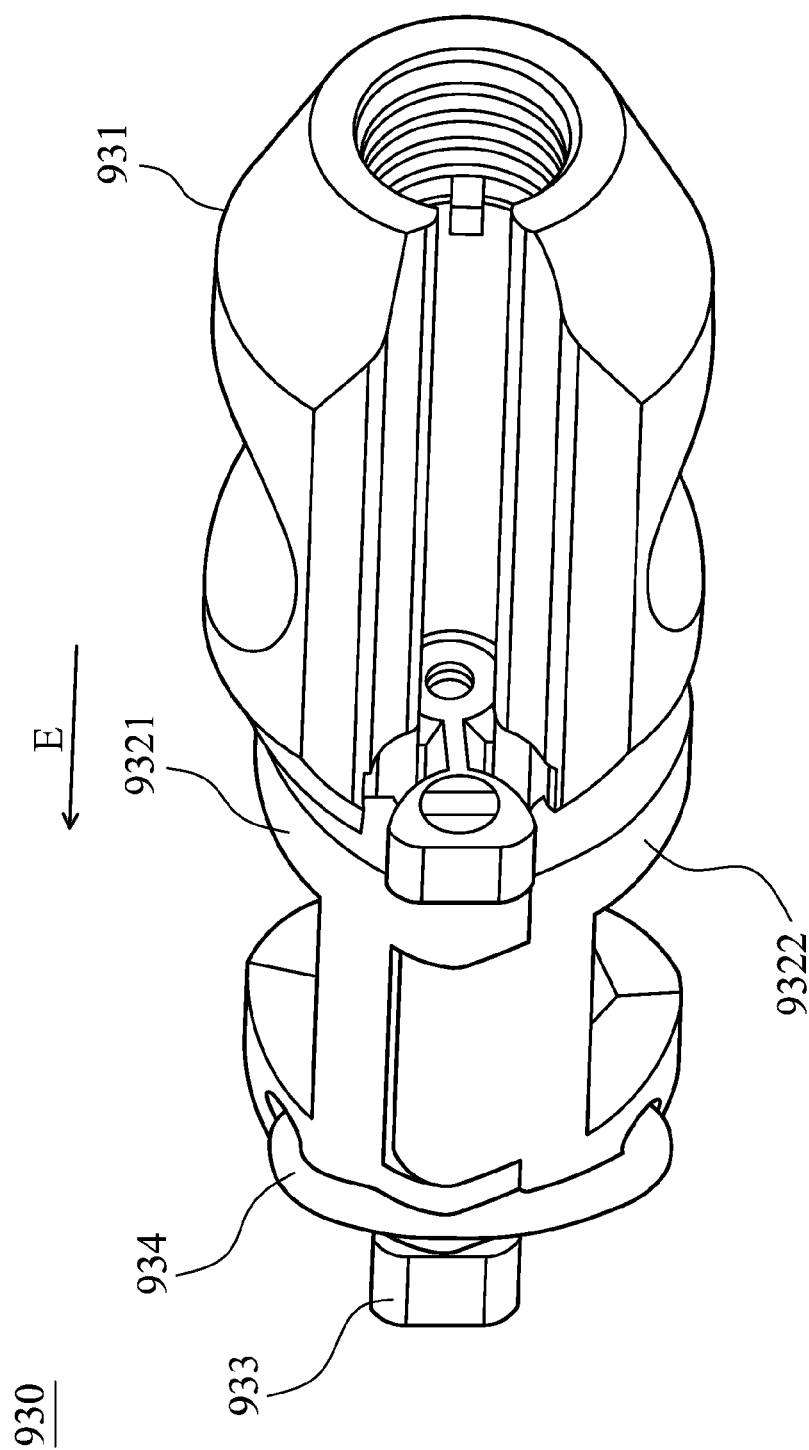
FIG. 18A is a schematic view showing a main portion relatively moving away from a foldable supporting structure of another embodiment of a spinal dynamic stabilization device of the invention
Figure 18B:
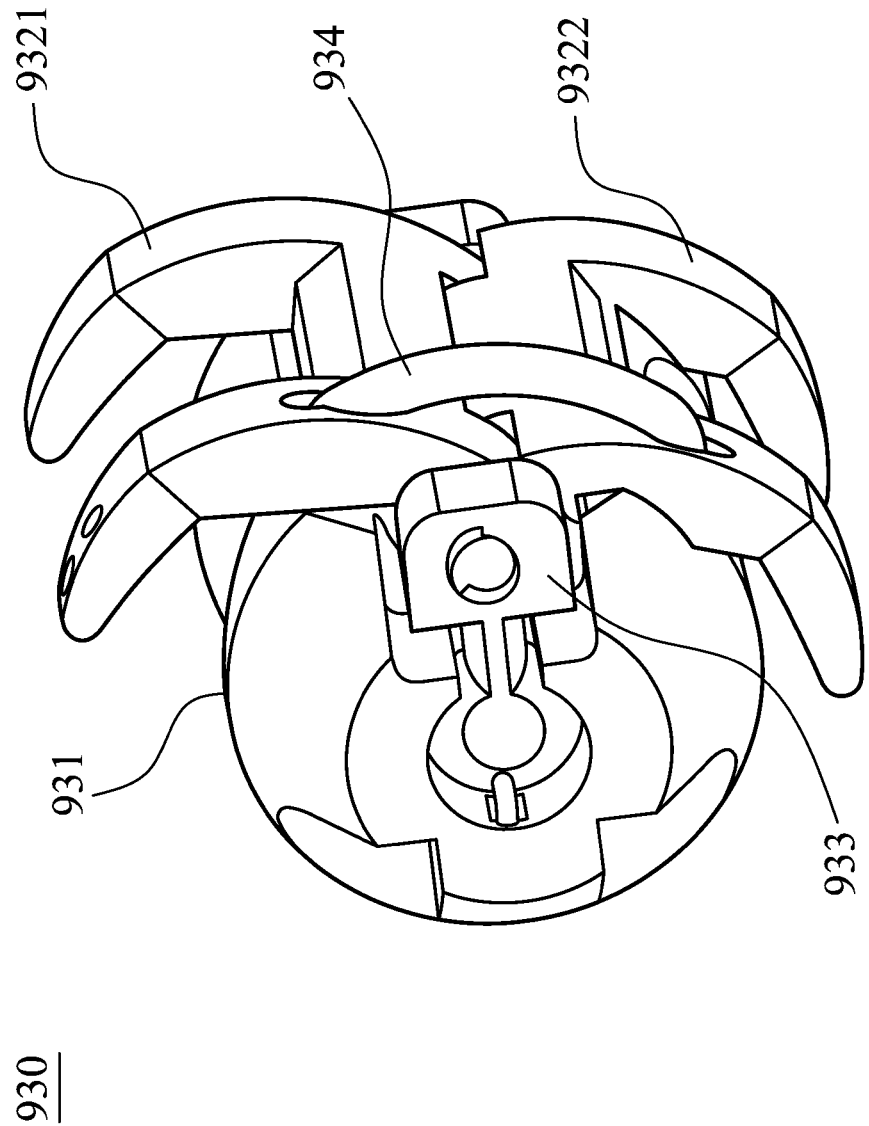
FIG. 18B is a schematic view showing a main portion relatively approaching a foldable supporting structure of another embodiment of a spinal dynamic stabilization device of the invention.

FIG. 18A is a schematic view showing a main portion relatively moving away from a foldable stabilizing portion of another embodiment of a spinal dynamic stabilization device of the invention. FIG. 18B is a schematic view showing a main portion relatively approaching a foldable stabilizing portion of another embodiment of a spinal dynamic stabilization device of the invention.

Referring to FIGS. 18A and 18B, this embodiment is approximately similar to the embodiment in FIG. 14. Thus, similar descriptions are omitted for brevity. The difference however, is that the spinal dynamic stabilization device 930 further comprises a shape memory alloy 934. The shape memory alloy 934 is disposed between the arm portions 9321 and 9322. In FIGS. 18A and 18B, the shape memory alloy 934 is in a stretched state. When the main portion 31 is pushed toward the arm portions 9321 and 9322 along an arrow E, the arm portions 9321 and 9322 are propped; at which time, the shape memory alloy 934 returns to an initial state.

Figure 19:
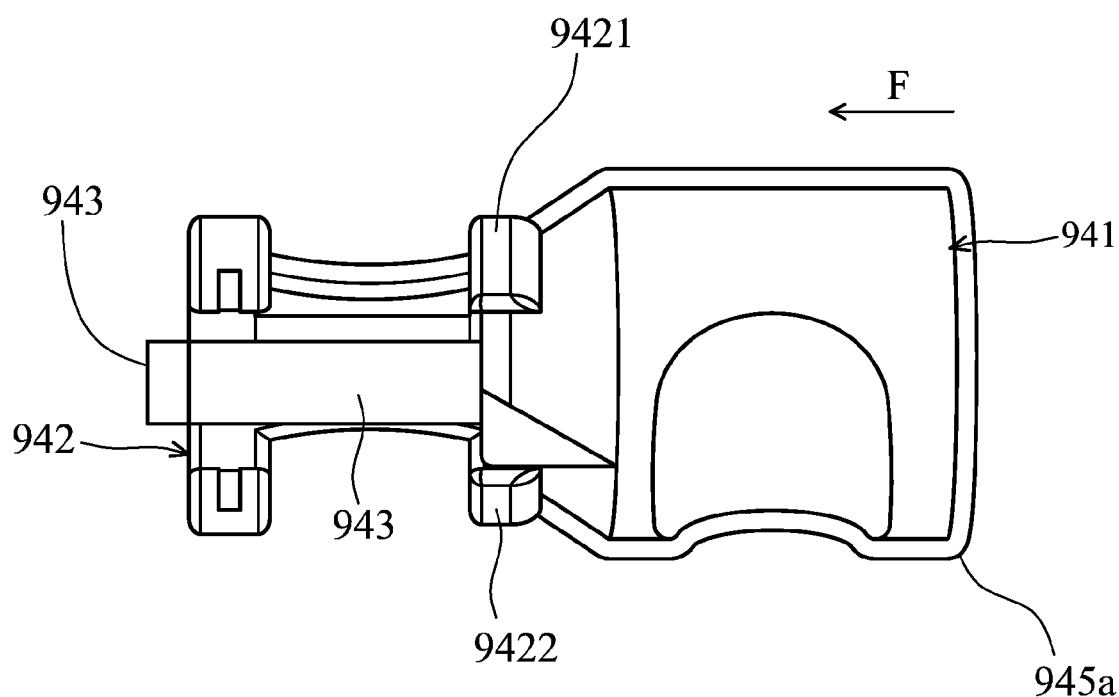
FIG. 19 is a schematic view showing another embodiment of a spinal dynamic stabilization device of the invention.
Figure 20:
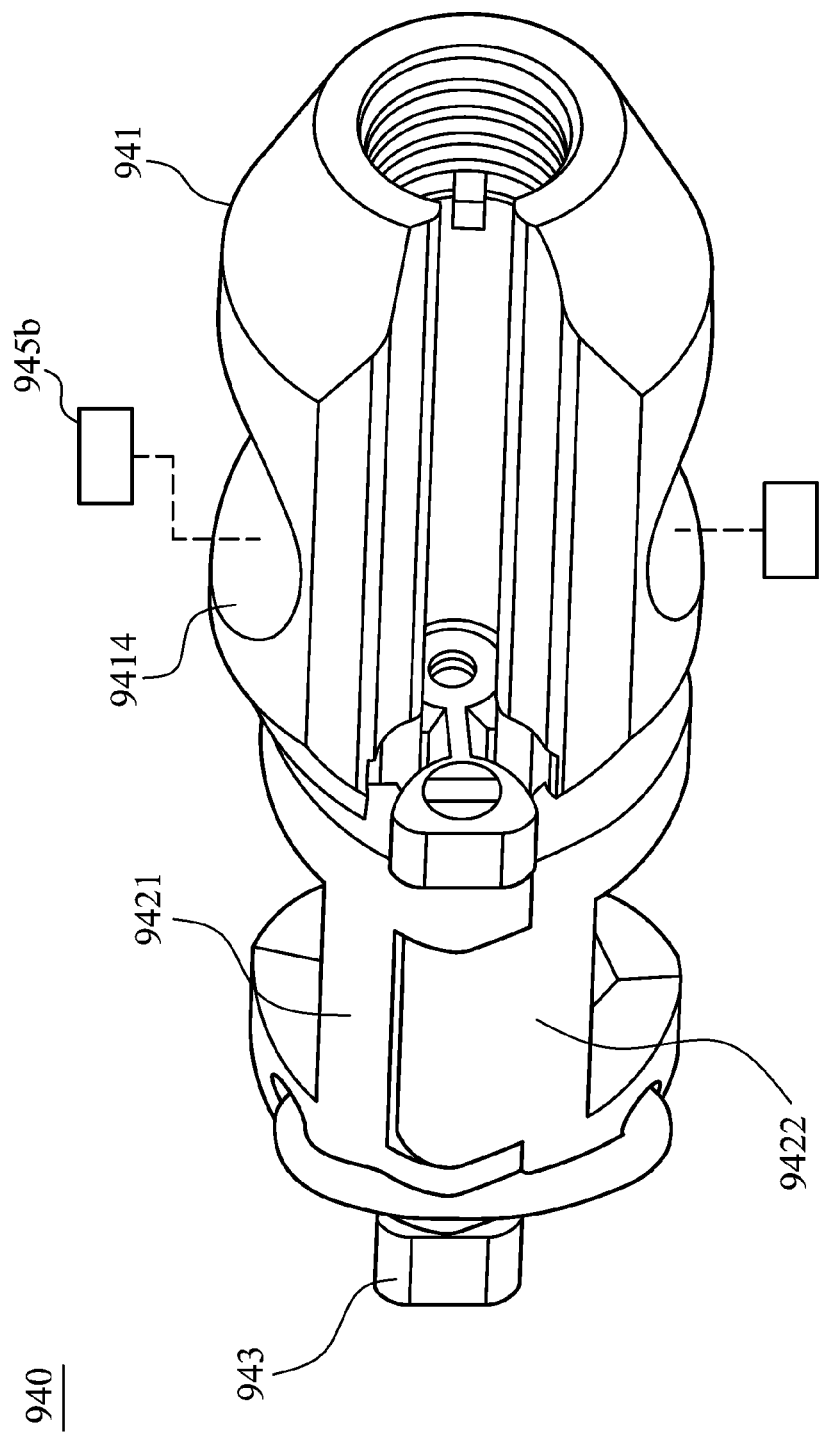
FIG. 20 is a schematic view showing another embodiment of a spinal dynamic stabilization device of the invention.

FIG. 19 is a schematic view showing another embodiment of a spinal dynamic stabilization device of the invention. FIG. 20 is a schematic view showing another embodiment of a spinal dynamic stabilization device of the invention. The embodiment in FIG. 19 is approximately similar to the embodiment in FIG. 14. Thus, similar descriptions are omitted for brevity. The difference however, is that the spinal dynamic stabilization device 940 further comprises a sensor 945a. The sensor 945a is disposed on the main portion 941 to react to pressure. The embodiment in FIG. 20 is approximately similar to the embodiment in FIG. 18A. Thus, similar descriptions are omitted for brevity. The difference however, the sensor 945b is disposed on the depression 9414 of the main portion 941.

Figure 21:
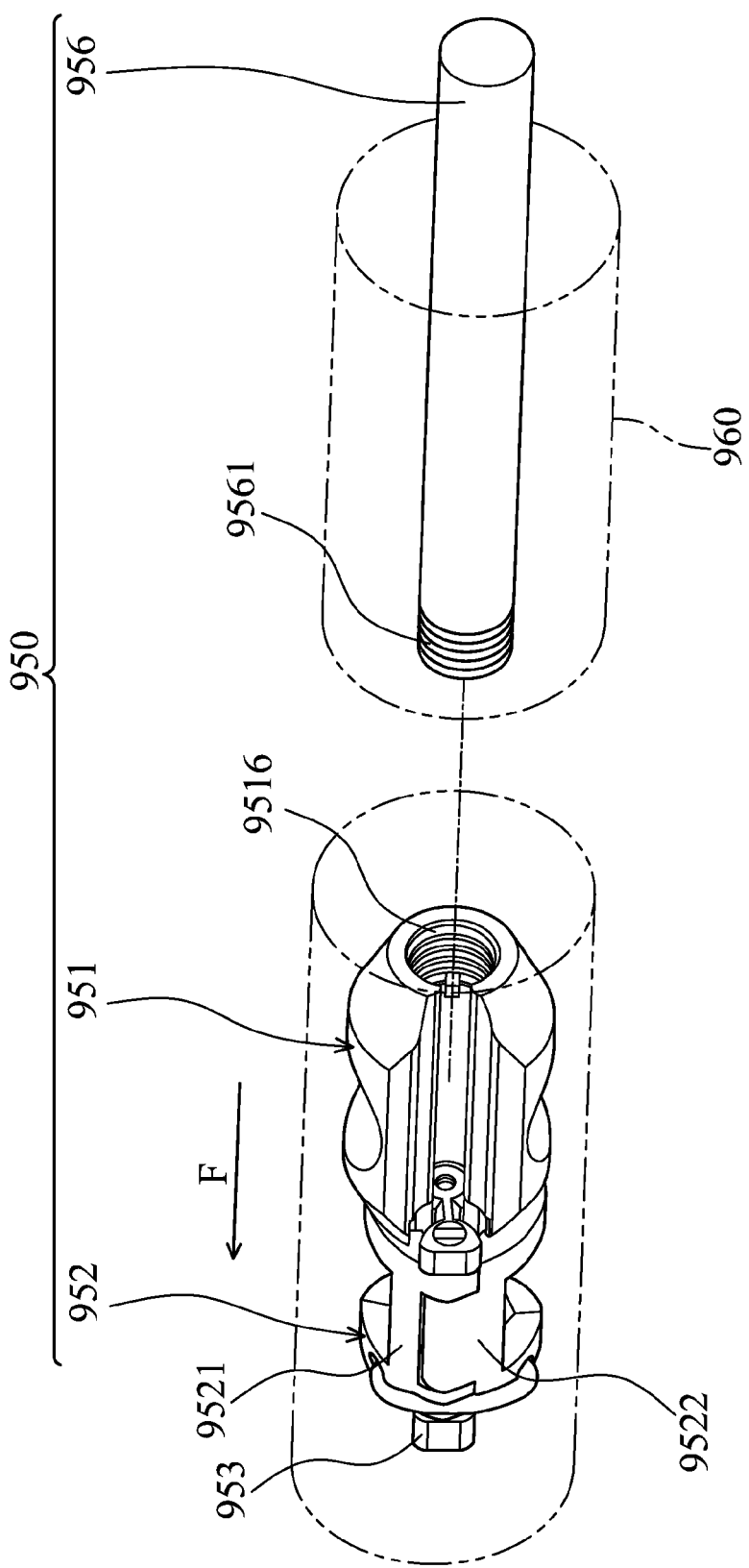
FIG. 21 is a schematic view showing a spinal dynamic stabilization device of the invention being pushed between adjacent vertebrae via a guiding tube.

FIG. 21 is a schematic view showing a spinal dynamic stabilization device of the invention being pushed between adjacent vertebrae via a guiding tube. Referring to FIG. 21, the spinal dynamic stabilization device 950 further comprises a guiding device 956. The guiding device 956 is a bar. One end comprises a first screw portion 9561. The main portion 951, the foldable stabilizing portion 952, and the sliding bar 953 are similar to the embodiment of FIG. 18A. When the main portion 951, the foldable stabilizing portion 952, and the sliding bar 953 enter a guiding tube 960, the first screw portion 9561 and the second screw portion 9516 are combined to provide the guiding device 956 to connect to the main portion 951. When the spinal dynamic stabilization device 950 reaches the adjacent vertebrae V (shown in FIG. 16), the main portion 951 is pushed via the guiding device 956 along an arrow F to prop up the arm portions 9521 and 9522 for maintaining normal physiological interval between the adjacent vertebrae V.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A spinal dynamic stabilization device, for implantation between adjacent vertebrae of a spine to distract the adjacent vertebrae, wherein the adjacent vertebrae have a sagittal plane, comprising:
   at least a main portion, comprising a guiding groove;
   at least a stabilizing portion, comprising two arm portions and a pivoting portion, wherein each of the two arm portions is connected to the pivoting portion and pivotable about an axis parallel to a longitudinal axis of the pivoting portion; and
   at least a sliding bar, connected to the pivoting portion and moveable along the guiding groove in a first direction parallel to the longitudinal axis;
   arranged such that movement of the sliding bar in the guiding groove in the first direction drives the arm portions to pivot from a posterior towards an anterior side of the spine.

2. The spinal dynamic stabilization device as claimed in claim 1, the main portion and the stabilization portion is detachable.

3. The spinal dynamic stabilization device as claimed in claim 1, wherein connection between the main portion and the stabilizing portion is not linear, or train-like arrangement.

4. The spinal dynamic stabilization device as claimed in claim 1, wherein connection between the main portion and the stabilizing portion include an angle, the angle is not equal to zero.

5. The spinal dynamic stabilization device as claimed in claim 1, wherein the device further comprises an engaging portion to engage the main portion and the stabilizing portion.

6. The spinal dynamic stabilization device as claimed in claim 1, wherein the main portion comprises a cone portion disposed on one end of the main portion.

7. The spinal dynamic stabilization device as claimed in claim 1, wherein the cross-section of the main portion is C-shaped.

8. The spinal dynamic stabilization device as claimed in claim 1, wherein the first direction is perpendicular to the sagittal plane.

9. The spinal dynamic stabilization device as claimed in claim 1, wherein the stabilizing portion is flexible.

10. The spinal dynamic stabilization device as claimed in claim 1, wherein the stabilizing portion is compressible.

11. The spinal dynamic stabilization device as claimed in claim 1, wherein the stabilizing portion is made of a compressible or damping material.

12. The spinal dynamic stabilization device as claimed in claim 1, wherein the arm portions of the stabilizing portion are curved.

13. The spinal dynamic stabilization device as claimed in claim 1, wherein the two arm portions are U, or H shaped.

14. The spinal dynamic stabilization device as claimed in claim 1, wherein at least one of the pivoting portions is hollow.

15. The spinal dynamic stabilization device as claimed in claim 1, wherein at least one of the pivoting portions is flexible.

16. A spinal dynamic stabilization device, for entering adjacent vertebrae of a spine via a guiding tube to maintain the normal physiological interval between the adjacent vertebrae, wherein the adjacent vertebrae have a sagittal plane, comprising:
    at least a main portion, comprising at least a guiding groove and a cone portion formed on one end of the main portion;
    at least a stabilizing portion, comprising arm portions, wherein the arm portions pivot in relation to each other; and
    a sliding bar, connected to the stabilizing portion and moveable in the guiding groove;
    arranged such that movement of the sliding portion in the guiding groove drives the cone portion to abut against the arm portions and drives the main portion to translate across the arm portions so that the arm portions are driven to rotatably expand toward the adjacent vertebrae of the spine.

17. The spinal dynamic stabilization device claimed in claim 16, further comprising at least a guiding element that is able to connect the main portion and the stabilizing portion to advance in a guiding tube.

18. The spinal dynamic stabilization device as claimed in claim 16, wherein the main portion and the stabilizing portion are detachable.

19. The spinal dynamic stabilization device claimed in claim 16, wherein movement of the main portion away from the stabilizing portion causes the stabilizing portion to enter a closed state, and movement of the main portion towards the stabilizing portion causes the stabilizing portion to enter an open state.

20. The spinal dynamic stabilization device as claimed in claim 16, wherein the main portion is an asymmetric cylinder.

21. The spinal dynamic stabilization device as claimed in claim 16, wherein the main portion is a cylinder.

22. The spinal dynamic stabilization device as claimed in claim 16, wherein the main portion further comprises saddles on sides thereof.

23. The spinal dynamic stabilization device as claimed in claim 16, wherein the main portion and the stabilizing portion are made of metal, polymer or biomaterials.

24. The spinal dynamic stabilization device as claimed in claim 16, wherein the main portion and the stabilizing portion are metal or nonmetal material coated with a flexible material, and the flexible material comprises macromolecular compounds or a flexible metal.

25. The spinal dynamic stabilization device as claimed in claim 16, wherein the main portion is a hollow structure, and the main portion is filled with a bone cement, a physiological solution or a flexible biological polymer material.

26. The spinal dynamic stabilization device as claimed in claim 16, further comprising a sensor, wherein the sensor is disposed on the main portion for reacting to pressure.

27. The spinal dynamic stabilization device as claimed in claim 16, wherein the arm portions are claw-type.

28. The spinal dynamic stabilization device as claimed in claim 16, wherein the stabilizing portion is a unitary structure and a foldable structure.

29. The spinal dynamic stabilization device as claimed in claim 16, wherein the arm portions are U-shaped.

30. The spinal dynamic stabilization device as claimed in claim 16, wherein the arm portions are H-type.

31. The spinal dynamic stabilization device as claimed in claim 16, wherein the stabilizing portion further comprises a pivoting portion, wherein the pivoting portion is connected to the sliding bar, and the arm portions are pivoted via the pivoting portion.

32. The spinal dynamic stabilization device as claimed in claim 16, wherein the sliding bar comprises an engaging portion, the engaging portion is disposed on one end of the sliding bar, and the engaging portion fixes the sliding bar to the main portion.

33. The spinal dynamic stabilization device as claimed in claim 16, wherein the main portion is a column.

34. The spinal dynamic stabilization device as claimed in claim 16, wherein the main portion further comprises saddle portions disposed on an upper side and a lower side of the main portion.

35. The spinal dynamic stabilization device as claimed in claim 16, wherein the main portion further comprises a flexible polymer to cover the main portion.

36. The spinal dynamic stabilization device as claimed in claim 16, further comprising a shape memory alloy wire disposed between the arm portions.

37. A spinal dynamic stabilization device, for implantation between adjacent vertebrae to distract the adjacent vertebrae, comprising:
    at least a main portion;
    at least a sliding bar movable relative to the main portion in a first direction; and
    at least a stabilizing portion, comprising two arm portions, and a pivoting portion connected to the sliding bar, wherein each of the two arm portions is connected to the pivoting portion and is pivotable about an axis parallel to a longitudinal axis of the pivoting portion, and the first direction is parallel to the longitudinal axis of the pivoting portion.

* * * * *